(12) United States Patent
Hirata et al.

(10) Patent No.: US 7,803,576 B2
(45) Date of Patent: Sep. 28, 2010

(54) NUCLEIC ACID SEQUENCES ENCODING VEGF-LIKE FACTORS AND USES THEREOF

(75) Inventors: Yuichi Hirata, Ibaraki (JP); Junichi Nezu, Ibaraki (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 995 days.

(21) Appl. No.: 11/397,289

(22) Filed: Apr. 4, 2006

(65) Prior Publication Data

US 2006/0172343 A1 Aug. 3, 2006

Related U.S. Application Data

(60) Continuation of application No. 10/978,107, filed on Oct. 29, 2004, now abandoned, which is a division of application No. 09/214,982, filed as application No. PCT/JP97/02456 on Jul. 15, 1997, now Pat. No. 6,828,426.

(30) Foreign Application Priority Data

Jul. 15, 1996 (JP) .................................. 8-185216

(51) Int. Cl.
*C12N 15/12* (2006.01)
*C12N 15/63* (2006.01)
*C12N 1/21* (2006.01)
*C12N 5/10* (2006.01)

(52) U.S. Cl. ................... 435/69.1; 435/243; 435/320.1; 435/325; 536/23.1; 536/23.5

(58) Field of Classification Search .................. None
See application file for complete search history.

(56) References Cited

U.S. PATENT DOCUMENTS

| | | | |
|---|---|---|---|
| 6,235,713 B1 | 5/2001 | Achen et al. | |
| 6,828,426 B1 | 12/2004 | Hirata et al. | |
| 2003/0114658 A1* | 6/2003 | Achen et al. | ............... 536/23.5 |

FOREIGN PATENT DOCUMENTS

| | | |
|---|---|---|
| CA | 2230957 | 4/1997 |
| EP | 0935001 A1 | 8/1999 |
| EP | 0 721 015 B1 | 10/2004 |
| WO | WO 94/10202 | 5/1994 |
| WO | WO 94/11499 | 5/1994 |
| WO | WO 94/21679 | 9/1994 |
| WO | WO 95/24473 | 9/1995 |
| WO | WO 97/05250 A2 | 2/1997 |
| WO | WO 97/09427 | 3/1997 |
| WO | WO 97/12972 | 4/1997 |
| WO | WO 98/07832 | 2/1998 |
| WO | WO 98/24811 | 6/1998 |

OTHER PUBLICATIONS

Kaufman et al. Blood. 94(9): 3178-3184, 1999.*
Wang et al. Nucleic Acids Research. 27(23): 4609-4618, 1999.*
Phillips, A. J. J. Pharm. Pharmacology. 53: 1169-1174, 2001.*
Achen et al., "Monoclonal Antibodies to Vascular Endothelial Growth Factor-D Block its Interactions with Both VEGF Receptor-2 and VEGF Receptor-3," *Eur. J. Biochem.* 267(9):2505-2515 (2000).
Crystal, "Transfer of Genes to Humans: Early Lessons and Obstacles to Success," *Science*, 270(5235):404-410 (1995).
Friedman, "Overcoming the Obstacles to Gene Therapy," *Sci. Am.*, 276(6):96-101 (1997).
GB Patent Application No. 9519928.7 (Sep. 29, 1995).
GB Patent Application No. 9612368.2 (Jun. 13, 1996).
Stacker et al., "Biosynthesis of Vascular Endothelial Growth Factor-D Involves Proteolytic Processing which Generates Non-Covalent Homodimers," *J. Biol. Chem.*, 274(45):32127-32136 (1999).
Witzenbichler et al., "Vascular Endothelial Growth Factor-C (VEGF-C/VEGF-2) Promotes Angiogenesis in the Setting of Tissue Ischemia," *Am. J.Path.* 153(2):381-394 (1998).
Breier et al., "Expression of vascular endothelial growth factor during embryonic angiogenesis and endothelial cell differentiation", *Development* 114:521-532 (1992).
Claffey et al., "Vascular endothelial growth factor. Regulation by cell differentiation and activated second messenger pathways", *J. Biol. Chem.* 267(23):16317-16322 (1992).
Conn et al., "Amino acid and cDNA sequences of a vascular endothelial cell mitogen that Is homologous to platelet-derived growth factor", *Proc. Natl. Acad. Sci. USA* 87:2628-2632 (1990).
Joukov et al., "A novel vascular endothelial growth factor, VEGF-C, is a ligand for the Flt4 (VEGFR-3) and KDR (VEGFR-2) receptor tyrosine kinases", *EMBO J.* 15(2):290-298 (1996).
Joukov et al., "A novel vascular endothelial growth factor, VEGF-C, is a ligand for the Flt4 (VEGFR-3) and KDR (VEGFR-2) receptor tyrosine kinases", *EMBO J.* 15(7):1751 (1996).
Marconcini et al., c-*fos*-induced growth factor/vascular endothelial growth factor D induces angiogenesis in vivo and in vitro, *Proc. Natl. Acad. Sci USA* 96:9671-9676 (1999).
Orlandini et al., "Identification of a c-*fos*-induced gene that is related to the platelet-derived growth factor/vascular endothelial growth factor family," *Proc. Natl. Acad. Sci. USA* 93:11675-11680 (1996).
Rocchigiani et al., "Human *FIGF*: cloning, gene structure, and mapping to chromosome Xp22.1 between the *PIGA* and the *GRPR* genes," *Genomics* 47:207-216 (1998).
Shima et al., "The mouse gene for vascular endothelial growth factor. Genomic structure, definition of the transcriptional unit, and characterization of transcriptional and post-transcriptional regulatory sequences", *J. Biol. Chem.* 271(7):3877-3883 (1996).
Tischer et al., "The human gene for vascular endothelial growth factor. Multiple protein forms are encoded through alternative exon splicing", *J. Biol. Chem.* 266(18):11947-11954 (1991).
Yamada et al., "Molecular cloning of a novel vascular endothelial growth factor, VEGF-D," *Genomics* 42:483-488 (1997).
Hillier et al., Database EMBL Online Accession No. H24828 (Jul. 8, 1995).

(Continued)

*Primary Examiner*—Christine J Saoud
(74) *Attorney, Agent, or Firm*—Clark & Elbing LLP

(57) ABSTRACT

The invention relates to VEGF-like nucleic acid sequences, their use, and vectors and transformants containing such sequences.

6 Claims, 4 Drawing Sheets

OTHER PUBLICATIONS

Hillier et al., GenBank Database Accession No. T64277 (Feb. 18, 1995).

Ludwig Institute for Cancer Research, Australian Patent Application Serial No. P07435, filed Jun. 19, 1997.

Yamada et al., GenBank Database Accession No. D89628 (Nov. 29, 1996).

Houck et al. "Dual Regulation of Vascular Endothelial Growth Factor Bioavailability by Genetic and Proteolytic Mechanisms," Journal of Biological Chemistry 267:26031-26037 (1992).

Lee et al. "Vascular Endothelial Growth Factor-Related Protein: A Ligand and Specific Activator of the Tyrosine Kinase Receptor Flt4," Proceedings of the National Academy of Sciences USA 93:1988-1992 (1996).

Achen et al., "Vascular endothelial growth factor D (VEGF-D) is a ligand for the tyrosine kinases VEGF receptor 2 (Flk1) and VEGF receptor 3 (Flt4)", *Proc. Natl. Acad. Sci. USA* 95(2):548-553 (1998).

Byzova et al., "Adenovirus encoding vascular endothelial growth factor-D induces tissue-specific vascular patterns in vivo", *Blood* 99(12):4434-4442 (2002).

Joukov et al., "Proteolytic processing regulates receptor specificity and activity of VEGF-C", *EMBO J.* 16(13):3898-3911 (1997).

Rissanen et al., "VEGF-D is the strongest angiogenic and lymphangiogenic effector among VEGFs delivered into skeletal muscle via adenoviruses", *Circ. Res.* 92(10):1098-1106 (2003).

Rutanen et al., "Adenoviral catheter-mediated intramyocardial gene transfer using the mature form of vascular endothelial growth factor-D induces transmural angiogenesis in porcine heart", *Circulation* 109(8):1029-1035 (2004).

Saaristo et al., "Vascular endothelial growth factor-C accelerates diabetic wound healing", *Am. J. Pathol*, 169(3):1080-1087 (2006).

Stacker et al., "VEGF-D promotes the metastatic spread of tumor cells via the lymphatics", *Nat. Med.* 7(2):186-191 (2001).

Amended pages of the specification of EP 0 956 339 B1 filed by the Patentee with Submissions, dated Oct. 3, 2008.

Communication from the European Patent Office issued with respect to EP 00 962 878.5, dated Apr. 26, 2004.

Li et al., "PDGF-C is a new protease-activated ligand for the PDGF α-receptor," *Nat Cell Biol.* 2: 302-309 (2000).

Minutes of the Oral Proceedings before the Opposition Division (Opposition of EP 97 938 486.4 by Chugai Seiyaku Kabushiki Kaisha), dated May 21, 2008.

Observations on the Patentee's proposed amendments to the specification of EP 0 956 339 B1, dated Dec. 17, 2008.

Response to the Communication from the European Patent Office issued with respect to EP 00 962 878.5 (dated Apr. 26, 2004), dated Sep. 20, 2004.

Smyth et al., "Conformational changes during proteolytic processing of a picornavirus capsid proteins," *Arch Virol.* 145: 1473-1479 (2000).

Specks, "What you should know about PR3-ANCA. Conformational requirements of proteinase 3 (PR3) for enzymatic activity and recognition by PR3-ANCA," *Arthritis Res.* 2: 263-267 (2000).

Kawatani and Imoto, "Deletion of the BH1 domain of Bcl-2 accelerates apoptosis by acting in a dominant negative fashion," *J Biol Chem.* 278: 19732-19742 (2003).

Reeck et al., "'Homology' in proteins and nucleic acids: a terminology muddle and a way out of it," *Cell* 50: 667 (1987).

Alignment of partial PDGF/VEGF family sequences (Exhibit D), cited in Reply to Annex Communication of Summons to Attend Oral Proceedings (Opposition of EP 97 93 8486.4 by Chugai Seiyaku Kabushiki Kaisha), dated Feb. 1, 2008.

Alignment of the VEGF-D coding sequences (Exhibit E), cited in Reply to Annex Communication of Summons to Attend Oral Proceedings (Opposition of EP 97 93 8486.4 by Chugai Seiyaku Kabushiki Kaisha), dated Feb. 1, 2008.

Alignment of the human and murine VEGF-D coding sequences (Exhibit F), cited in Reply to Annex Communication of Summons to Attend Oral Proceedings (Opposition of EP 97 93 8486.4 by Chugai Seiyaku Kabushiki Kaisha), dated Feb. 1, 2008.

Claim Requests submitted by the Patentee during Oral Proceedings (Opposition of EP 97 93 8486.4 by Chugai Seiyaku Kabushiki Kaisha), held on Apr. 3, 2008.

D11, D12, and D19, cited in Reply to Written Opposition (Opposition of EP 97 93 8486.4 by Chugai Seiyaku Kabushiki Kaisha), dated Feb. 28, 2007.

Drawings submitted by the Opponent (Chugai) during Oral Proceedings (Opposition of EP 97 93 8486.4 by Chugai Seiyaku Kabushiki Kaisha), held on Apr. 3, 2008.

Exhibits A to C, cited in Written Opposition (Opposition of EP 97 93 8486.4 by Chugai Seiyaku Kabushiki Kaisha), dated Jul. 12, 2006.

Hannink et al., "Deletions in the C-Terminal Coding Region of the v-*sis* Gene: Dimerization Is Required for Transformation," *Mol Cell Biol.* 6(4): 1304-1314 (1986).

Heldin et al., "Structure of Platelet-Derived Growth Factor: Implications for Functional Properties," *Growth Factors* 8(4): 245-252 (1993).

Keck et al., "Vascular Permeability Factor, an Endothelial Cell Mitogen Related to PDGF," *Science* 246(4935): 1309-1312 (1989).

Leung et al., "Vascular Endothelial Growth Factor Is a Secreted Angiogenic Mitogen," *Science* 246(4935): 1306-1309 (1989).

Mishell et al., "Fluorescent Antibodies," from "Selected Methods in Cellular Immunology" (Eds. Mishell, BB and Shiigi, SM), W.H. Freeman and Co., San Francisco, pp. 292-297, 1980.

Nakane, "Localization of Hormones with the Peroxidase-Labeled Antibody Method," *Methods Enzymol.* 37(Pt. B): 133-144 (1975).

Notice of Opposition of EP 97 93 8486.4 by Chugai Seiyaku Kabushiki Kaisha, dated Jul. 12, 2006.

Olofsson et al., "Vascular Endothelial Growth Factor B, a Novel Growth Factor for Endothelial Cells," *Proc Natl Acad Sci USA* 93(6): 2576-2581 (1996).

Östman et al., "Synthesis and Assembly of a Functionally Active Recombinant Platelet-Derived Growth Factor AB Heterodimer," *J Biol Chem.* 263(31): 16202-16208 (1988).

Östman et al., "PDGF-AA and PDGF-BB Biosynthesis: Proprotein Processing in the Golgi Complex and Lysosomal Degradation of PDGF-BB Retained Intracellulariy," *J Cell Biol.* 118(3): 509-519 (1992).

Reply to Annex Communication of Summons to Attend Oral Proceedings (Opposition of EP 97 93 8486.4 by Chugai Seiyaku Kabushiki Kaisha), dated Feb. 1, 2008.

Reply to Reply to Annex Communication of Summons to Attend Oral Proceedings (Opposition of EP 97 93 8486.4 by Chugai Seiyaku Kabushiki Kaisha), dated Mar. 26, 2008.

Reply to Written Opposition (Opposition of EP 97 93 8486.4 by Chugai Seiyaku Kabushiki Kaisha), dated Feb. 28, 2007.

Sauer et al., "Deletions in the N-Terminal Coding Region of the v-*sis* Gene: Determination of the Minimal Transforming Region," *J Virol.* 59(2): 292-300 (1986).

Summons to Attend Oral Proceedings (Opposition of EP 97 93 8486.4 by Chugai Seiyaku Kabushiki Kaisha), dated Jun. 1, 2007.

Translation of Japanese Patent Application No. 8-185216, dated Jul. 10, 2000.

Notice of Opposition of European Patent No. 0935001 B1 by Ludwig Institute for Cancer Research, dated Feb. 3, 2006.

Annexes I to VI cited in Written Opposition (Opposition of European Patent No. 0935001 B1), dated Feb. 3, 2006.

Reply to Written Opposition (Opposition of European Patent No. 0935001 B1), dated Sep. 20, 2006.

Exhibit A cited in Reply to Written Opposition (Opposition of European Patent No. 0935001 B1), dated Sep. 20, 2006.

Response to Reply to Written Opposition (Opposition of European Patent No. 0935001 B1), dated Mar. 27, 2007.

Annexes VI to XII cited in Response to Reply to Written Opposition (Opposition of European Patent No. 0935001 B1), dated Mar. 27, 2007.

Summons to Attend Oral Proceedings for European Patent No. 0935001 B1, dated Mar. 3, 2008.

Patentee's Reply to Annex Communication of Summons to Attend Oral Proceedings for European Patent No. 0935001 B1, dated Dec. 15, 2008.

Documents D26 and D28 through D34 cited in Patentee's Reply to Annex Communication of Summons to Attend Oral Proceedings for European Patent No. 0935001 B1, dated Dec. 15, 2008.
Opponent's Reply to Annex Communication of Summons to Attend Oral Proceedings for European Patent No. 0935001 B1, dated Dec. 15, 2008.
Documents D25 and D28 cited in Opponent's Reply to Annex Communication of Summons to Attend Oral Proceedings for European Patent No. 0935001 B1, dated Dec. 15, 2008.
Minutes of the Oral Proceedings for European Patent No. 0935001 B1, dated Apr. 16, 2009.
Interlocutory Decision in Opposition Proceedings for European Patent No. 0935001 B1, dated Apr. 16, 2009.
Interlocutory Decision in Opposition Proceedings (Opposition of EP 97 93 8486.4 by Chugai Seiyaku Kabushiki Kaisha) dated Apr. 28, 2009.
U.S. Appl. No. 08/671,573, filed Jun. 28, 1996, Alitalo and Joukov.
Baldwin et al., "The specificity of receptor binding by vascular endothelial growth factor-D is different in mouse and man," *J. Biol. Chem.* 276(22):19166-71 (2001).
Bywater et al., "Expression of recombinant platelet-derived growth factor A- and B-chain homodimers in Rat-1 cells and human fibroblasts reveals differences in protein processing and autocrine effects," *Mol. Cell Biol.* 8(7):2753-62 (1988).
Conn and Stumpf, Outlines of biochemistry ($4^{th}$ edition), Section 4.3:75-7 (1976).
Ferrara et al., "Molecular and biological properties of the vascular endothelial growth factor family of proteins," *Endocrine Rev.* 13(1):18-32 (1992).
Maglione et al., "Isolation of a human placenta cDNA coding for a protein related to the vascular permeability factor," *PNAS* 88(20):9267-71 (1991).
McDonald and Hendrickson, "A structural superfamily of growth factors containing a cystine knot motif," *Cell* 73(3):421-4 (1993).
Olofsson et al., "Genomic organization of the mouse and human genes for vascular endothelial growth factor B (VEGF-B) and characterization of a second splice isoform," *J. Biol. Chem.* 271(32):19310-7 (1996).
Park et al., "Placenta growth factor: potentiation of vascular endothelial growth factor bioactivity, in vitro and in vivo, and high affinity binding to Flt-1 but not to Flk-1/KDR," *J. Biol. Chem.* 269(41):25646-54 (1994).
Interference Initial Memorandum, Interference No. 105,695, dated May 21, 2009, Achen (U.S. Appl. No. 11/304,585) and Hirata (U.S. Appl. No. 11/397,289).
Notice to Declare Interference, Interference No. 105,695, dated Aug. 26, 2009, Achen (U.S. Appl. No. 11/304,585) and Hirata (U.S. Appl. No. 11/397,289).
Hirata Motion 1—For Judgment Based on Estoppel, Interference No. 105,695, dated Dec. 3, 2009, Achen (U.S. Appl. No. 11/304,585) and Hirata (U.S. Appl. No. 11/397,289).
Hirata Exhibit 1035, Declaration of Frederick M. Ausubel, Ph.D., Interference No. 105,695, dated Dec. 3, 2009, Achen (U.S. Appl. No. 11/304,585) and Hirata (U.S. Appl. No. 11/397,289).
Abandonment of Contest by Junior Party Achen et al., Interference No. 105,695, dated Jan. 5, 2010, Achen (U.S. Appl. No. 11/304,585) and Hirata (U.S. Appl. No. 11/397,289).
Judgment—Request for Adverse—Bd.R. 127(b), Interference No. 105,695, dated Jan. 6, 2010, Achen (U.S. Appl. No. 11/304,585) and Hirata (U.S. Appl. No. 11/397,289).
Notice to Declare Interference, Interference No. 105,098, dated Apr. 3, 2003, Achen (U.S. Patent No. 6,235,713) and Hirata (U.S. Appl. No. 09/214,892).
Achen Request for Entry of Adverse Judgment, Interference No. 105,098, dated Oct. 13, 2003, Achen (U.S. Patent No. 6,235,713) and Hirata (U.S. Appl. No. 09/214,892).
Judgment Pursuant to 37 CFR § 1.662, Interference No. 105,098, dated Oct. 23, 2003, Achen (U.S. Patent No. 6,235,713) and Hirata (U.S. Appl. No. 09/214,892).
Demir et al., "Vasculogenesis and angiogenesis in the early human placenta," *Acta Histochemica* 109:257-265, 2007.
Folkman et al., "Angiogenesis," *J Biol Chem* 267:10931-10934, 1992.

Letter from the National Library of Medicine in Bethesda, MD, U.S.A., dated Mar. 3, 2010.
Notice of Opposition against EP Patent No. 1749836, European Patent Office, dated Mar. 17, 2010.
Risau et al., "Vasculogenesis and angiogenesis in embryonic-stem-cell-derived embryoid bodies," *Development* 102:471-478, 1988.
Risau, "Differentiation of endothelium," *FASEB J* 9:926-933, 1995.
Achen et al., "Vascular Endothelial Growth Factor D (VEGF-D) is a Ligand for the Tyrosine Kinases VEGF Receptor 2 (Flk1) and VEGF Receptor 3 (Flt4)," *Proc. Natl. Acad. Sci. U.S.A.* 95:548-553, 1998.
Asahara et al., "Bone Marrow Origin of Endothelial Progenitor Cells Responsible for Postnatal Vasculogenesis in Physiological and Pathological Neovascularization," *Circ. Res.* 85:221-228, 1999.
Baldwin et al., "Vascular Endothelial Growth Factor D is Dispensable for Development of the Lymphatic System," *Mol. Cell. Biol.* 25:2441-2449, 2005.
Carmeliet et al., "Abnormal Blood Vessel Development and Lethality in Embryos Lacking a Single VEGF Allele," *Nature* 380:435-439, 1996.
Communication from Patentee (Universita Degli Studi Di Siena) Regarding European Patent No. 0853668, European Patent Office, dated May 12, 2009.
Decision Revoking the European Patent (European Patent No. EP0751992), European Patent Office, The Opposition Division, dated Jan. 30, 2009.
Experiments carried out by Achen and Stacker and Ludwig Institute for Cancer Research staffs, "Appendix 1: Fibroblast Assay Data Relating to Sienna—Experiment with Human FIGF/VEGF-D," as filed with the European Patent Office, dated Sep. 8, 2009.
Experiments carried out by Achen and Stacker and Ludwig Institute for Cancer Research staffs, "Appendix 2: Fibroblast Assay Data Relating to Sienna—Experiment with Mouse VEGF-D on Fibroblasts," as filed with the European Patent Office, dated Sep. 8, 2009.
Gray et al., "Growth Factors for Human Fibroblasts in the Solute Remaining After Clot Formation," *J. Cell. Sci.* 96:271-274, 1990.
Grzeszkiewicz et al., "CYR61 Stimulates Human Skin Fibroblast Migration through Integrin $\alpha_v\beta_5$ and Enhances Mitogenesis through Integrin $\alpha_v\beta_3$, Independent of its Carboxyl-Terminal Domain," *J. Biol. Chem.* 276:21943-21950, 2001.
Haiko et al., "Deletion of Vascular Endothelial Growth Factor C (VEGF-C) and VEGF-D is Not Equivalent to VEGF Receptor 3 Deletion in Mouse Embryos," *Mol. Cell. Biol.* 28:4843-4850, 2008.
Interlocutory Decision in Opposition Proceedings, European Application No. 97938486.4, European Patent Office, dated Apr. 28, 2009, p. 12.
Isner et al., "Angiogenesis and Vasculogenesis as Therapeutic Strategies for Postnatal Neovascularization," *J. Clin. Invest.* 103:1231-1236, 1999.
Karkkainen et al., "Vascular Endothelial Growth Factor C is Required for Sprouting of the First Lymphatic Vessels from Embryonic Veins," *Nat. Immunol.* 5:74-80, 2004.
Marconcini et al., "c-fos-Induced Growth Factor/Vascular Endothelial Growth Factor D Induces Angiogenesis in vivo and in vitro," *Proc. Natl. Acad. Sci. U.S.A.* 96:9671-9676, 1999.
Marked version of European Patent Application No. EP 97 93 0804.6, as filed on Feb. 15, 1999, showing comparision with priority document.
McColl et al., "Proprotein Convertases Promote Processing of VEGF-D, A Critical Step for Binding the Angiogenic Receptor VEGFR-2," *FASEB J.* 21:1088-1098, 2007.
Opponent's Statement of Grounds of Appeal Against Interlocutory Decision of the Opposition Division (Opposition of European Patent EP0935001), European Patent Office, dated Aug. 24, 2009.
Opponent's Statement of Grounds of Appeal Against Interlocutory Decision of the Opposition Division (Opposition of European Application No. 97938486.4), European Patent Office, dated Sep. 8, 2009.
Patentee's Statement of Grounds of Appeal Against Interlocutory Decision of the Opposition Division (Opposition of European Patent No. EP0956339), European Patent Office, dated Sep. 8, 2009.
Sakamaki et al., "Ligand-Dependent Activation of Chimeric Receptors with the Cytoplasmic Domain of the Interleukin-3 Receptor Beta Subunit (β IL3)," *J. Biol. Chem.* 268:15833-15839, 1993.

Tettamanti et al., "The Multifunctional Role of Fibroblasts During Wound Healing in *Hirudo medicinalis* (Annelida, Hirudinea)," *Biol. Cell* 96:443-455, 2004.

Toivanen et al., "Novel Vascular Endothelial Growth Factor D Variants with Increased Biological Activity," *J. Biol. Chem.* 284:16037-16048, 2009.

Baldwin et al., "Multiple Forms of Mouse Vascular Endothelial Growth Factor-D are Generated by RNA Splicing and Proteolysis," *J. Biol. Chem.* 276:44307-44314, 2001.

Hughes, "Alternative Splicing of the Human VEGFGR-3/FLT4 Gene as a Consequence of an Integrated Human Endogenous Retrovirus," *J. Mol. Evol.* 53:77-79, 2001.

Kaipainen et al., "Expression of the fms-like Tyrosine Kinase 4 Gene Becomes Restricted to Lymphatic Endothelium During Development," *Proc. Natl. Acad. Sci. USA* 92:3566-3570, 1995.

Shalaby et al., "Failure of Blood-Island Formation and Vasculogenesis in Flk-1-Deficient Mice," *Nature* 376:62-66, 1995.

Stacker et al., "A Mutant Form of Vascular Endothelial Growth Factor (VEGF) that Lacks VEGF Receptor-2 Activation Retains the Ability to Induce Vascular Permeability," *J. Biol. Chem.* 274:34884-34892, 1999.

Opponent's Reply to Grounds of Appeal (Opposition of European Patent No. EP0956339), European Patent Office, dated Jan. 27, 2010.

Patentee's Reply to Grounds of Appeal (Opposition of European Patent No. EP0956339), European Patent Office, dated Jan. 27, 2010.

Patentee's Reply to Grounds of Appeal (Opposition of European Patent No. EP0935001), European Patent Office, dated Feb. 10, 2010.

* cited by examiner

Fig. 2

```
SEQ ID NO: 29 HSVEGFCC*    MHLLGFFSVA CSLLAAALLP GPREAPAAAA AFESGLDLSD AEPDAGEATA    50
SEQ ID NO: 28 H24828       ---------- ---------- ---------- ---------- ----------    50

HSVEGFCC          YASKDLEEQL RSVSSVDELM TVLYPEYWKM YKCQLRKGGW QHNREQANLN    100
         H24828            ---------- ---------- ---------- ---------- ----------    100

HSVEGFCC          SRTEETIKFA AAHYNTEILK SIDNEWRKTQ CMPREVCIDV GKEFGVATNT    150
         H24828            ---------- ---------- ---------- ---------- ----------    150

HSVEGFCC          FFKPPCVSVY RCGGCCNSEG LQCMNTSTSY LSKTLFEITV PLSQGPKPVT    200
         H24828            ---------- ---------- ---------- ---------- ----------    200

HSVEGFCC          ISFANHTSCR CMSKLDVYRQ VHSIIRRSLP ATLPQCQAAN KTCPTNYMWN    250
         H24828            ---------- ---------- ---------- ---------- ----------    250

HSVEGFCC          NHICRCLAQE DFMFSSDAGD DSTDGFHDIC GPNKELDEET CQCVCRAGLR    300
         H24828            ---------- ---------- ---------- ---------- ------HLQE    300

HSVEGFCC          PASCGPHKEL CRNSCQCVCK NKLFPSQCGA NREFDENTCQ CVCKRTCPRN    350
         H24828            PALCGPHMMF DEDRCECVCK TPCPKDLIQH PKNCSCFEDK ESLETCCQKH    350

HSVEGFCC          QPLNPGKCAC ECTESPQKCL LKGKKFHHQT CSCYRRPCTN RQKAC-EPGF    400
         H24828            KLFHPDTCSC E--------- --------DR CPFHTRPCAS GKTACAKHCR    400

HSVEGFCC          SYSEEVCRCV CSYWRRPQMS .......... .......... ..........    450
         H24828            FPKEKRAAQG CHSRKNP... .......... .......... ..........    450

*HSVEGFCC:        human VEGF-C
```

Fig. 3

```
SEQ ID NO:1  HSVEGF-D    GYREWVVVNV FMMLYVQLVQ GSSNEHGPVK ---------- ------RSSQ    50
SEQ ID NO:29 HSVEGF-C    MHLLGFFSVA CSLLAAALLP GPREAPAAAA AFESGLDLSD AEPDAGEATA    50
SEQ ID NO:30 HSPDGF-A    MRTLACLLLL GCGYLAHVLA EEAEIPREVI ERLAR----- -------SQ     50
SEQ ID NO:31 HSPDGF-B    MNRCWALFLS LCCYLRLVSA EGDPIPEELY EMLSD----- --------HS    50
SEQ ID NO:32 HSPIGF2     MPVMRLFPCF LQLLAGLALP AVPPQQWALS AGNGS----- ----------    50
SEQ ID NO:33 HSVEGF      MNFLLSWVHW SLALLYLHH AKWSQAAPMA EGGGQ----- ----------    50
SEQ ID NO:34 HSVEGF-B    MSPLLRR--- --LLLAALLQ LAPAQAPVSQ PDAPG----- ----------    50

HSVEGF-D    STLERSELQI RAASSLELLL RIIHSEDWKL WRCRLRLKSF TSMDSRSASH   100
             HSVEGF-C    YASKDLEEQL RSVSSVDELM TVLYPEYWKM YKCQLRKGGW QHNREQANLN   100
             HSPDGF-A    IHSIRDLCRL LEIDSVGSED S-L------- ---------- ----DTSLRA   100
             HSPDGF-B    IRSFDDLCRL LHGDPGEEDG AEL------- ---------- ----DLNMTR   100
             HSPIGF2     ---------- ---------- ---------- ---------- ----------   100
             HSVEGF      ---------- ---------- ---------- ---------- ----------   100
             HSVEGF-B    ---------- ---------- ---------- ---------- ----------   100

HSVEGF-D    RST----RFA ATFYDIETLK VIDEEWQRTQ CSPRETCVEV ASELGKSINT   150
             HSVEGF-C    SRTEEDIKFA AAHYNTEILK SIDNEWRKTQ CMPREVCIDV GKEFGVAINT   150
             HSPDGF-A    HGVHALKHVP EKRPLPIRRK RSIEEAVPAV CKTRTVIYEI PRSQVDPLSA   150
             HSPDGF-B    SHSGGELESL ARGRRSLGSL TLAEPAMIAE CKTRIEVEEI SRRLIDRLNA   150
             HSPIGF2     ---------- ---SEVEVVP FQFV-WGRSY CRALERLVDV VSEYPSEVEH   150
             HSVEGF      ---------- ---NHHEVVK FMDV-YQRSY CHPIETLVDI FQEYPDEIEY   150
             HSVEGF-B    ---------- ---HQRKVVS WIDV-YTRAT CQPREVVVPL TVELMGTVAK   150

HSVEGF-D    FE--KPPCVN VFRCGGCCNE ESLICMNTST SYISKQLFEI -SVPLTSVPE   200
             HSVEGF-C    FF--KPPCVS VYRCGGCCNS EGLQCMNTST SYLSKTLFEI -TVPLSQGPK   200
             HSPDGF-A    NELIWPPCVE VKRCTGCCNT SSVKCQPSRV HHRSVKVAKV EYVRKKPKLK   200
             HSPDGF-B    NFLVWPPCVE VQRCSGCCNN RNVQCRPTQV QLRPVCVRKI EIVRKKPIFK   200
             HSPIGF2     MF--SPSCVS LLRCTGCCGD ENLHCVPVET ANVTMCLLKI ---RSGDRPS   200
             HSVEGF      IF--KPSCVP LMRCGGCCND EGLECVPTEE SNITMCIMRI ---KPHQGQH   200
             HSVEGF-B    QL--VPSCVT VQRCGGCCPD DGLECVPTGQ HQVRMCILMI ----RYPSSQ-   200

HSVEGF-D    LVPVKVANHT GCKCLPT--A PRHPYSIIRR SIQIPEEDRC SHSKKLCPID   250
             HSVEGF-C    PVTISFANHT SCRCMSKLDV YRQVHSIIRR S-LPATLPQC QAANKTCPIN   250
             HSPDGF-A    ELQVRLEEHL ECACATTSLN PDYREEDTGR P-RESGKRRK R--KRLKPT.   250
             HSPDGF-B    KATVTLEDHL ACKCEI-VAA ARPVTRSPGG S-QEQRAK-- ----------   250
             HSPIGF2     YVELTFSQHV RCECRP---- LREKMKPERR R-PKGRGKRR R--ERQRPT-   250
             HSVEGF      IGEMSFLQHN KCECRPKKD RARQEKKSVR G-KGKGQKRK R--KKSRYK-   250
             HSVEGF-B    LGEMSLEEHS QCECRPKKKD SA-------- ---------- ----------   250

HSVEGF-D    MLWDSNKCKC VLQEE-NPLA GTEDHSHLQE ---------- ----------   300
             HSVEGF-C    YMNNHICRC LAQEDFKFSS DAGDDSTDGF HDICGPNKEL EEETCQEVER   300
             HSPDGF-A    .......... .......... .......... .......... ..........   300
             HSPDGF-B    .......... .......... .......... .......... TPQTRVTIRT   300
             HSPIGF2     ---------- ---------- --DCHLCGDA VPRR...... ..........   300
             HSVEGF      ----SWSVYV GARCCLMFWS LPGPLPCGPC SERRKHLFVQ DPQTCKCSCK   300
             HSVEGF-B    ---------- ---------- VKPDSPRPLC PRCTQHHQRP DPRTCRCRCR   300

HSVEGF-D    ----PALCGP FMMFDEDRCE CVCKTPCPKD LIQHPKNCSC FECKESL-ET   350
             HSVEGF-C    AGLRPASCGP LKELDRNSCQ CVCKNKLFPS QCGANREFDE NTCQCVCKRT   350
             HSPDGF-A    .......... .......... .......... .......... ..........   350
             HSPDGF-B    VRVRRPPKGK ERKFKHTHDK TALKETLGA. .......... ..........   350
             HSPIGF2     .......... .......... .......... .......... ..........   350
             HSVEGF      N-TDSRCKAR QLELNERTCR CDKPRR.... .......... ..........   350
             HSVEGF-B    RRSFLRCQGR GLELNPDTCR CRKLRR.... .......... ..........   350

HSVEGF-D    CCQKHKLFHP DTCSCE---- ---------- ---DRCPFHT RPCASGKTAC   400
             HSVEGF-C    CPRNQPL-NP GKLACECTES PQKCLLKGKK FHHQTCSCYR RPCTNRQKAC   400
             HSPDGF-A    .......... .......... .......... .......... ..........   400
             HSPDGF-B    .......... .......... .......... .......... ..........   400
             HSPIGF2     .......... .......... .......... .......... ..........   400
             HSVEGF      .......... .......... .......... .......... ..........   400
             HSVEGF-B    .......... .......... .......... .......... ..........   400

HSVEGF-D    AKHCRFPKEK RAAQGPHSRK NP........ .......... ..........   450
             HSVEGF-C    -EPGFSYSEE VCRCVPSYWK RPQMS..... .......... ..........   450
             HSPDGF-A    .......... .......... .......... .......... ..........   450
             HSPDGF-B    .......... .......... .......... .......... ..........   450
             HSPIGF2     .......... .......... .......... .......... ..........   450
             HSVEGF      .......... .......... .......... .......... ..........   450
             HSVEGF-B    .......... .......... .......... .......... ..........   450
```

Fig. 4
A) Hydrophobicity
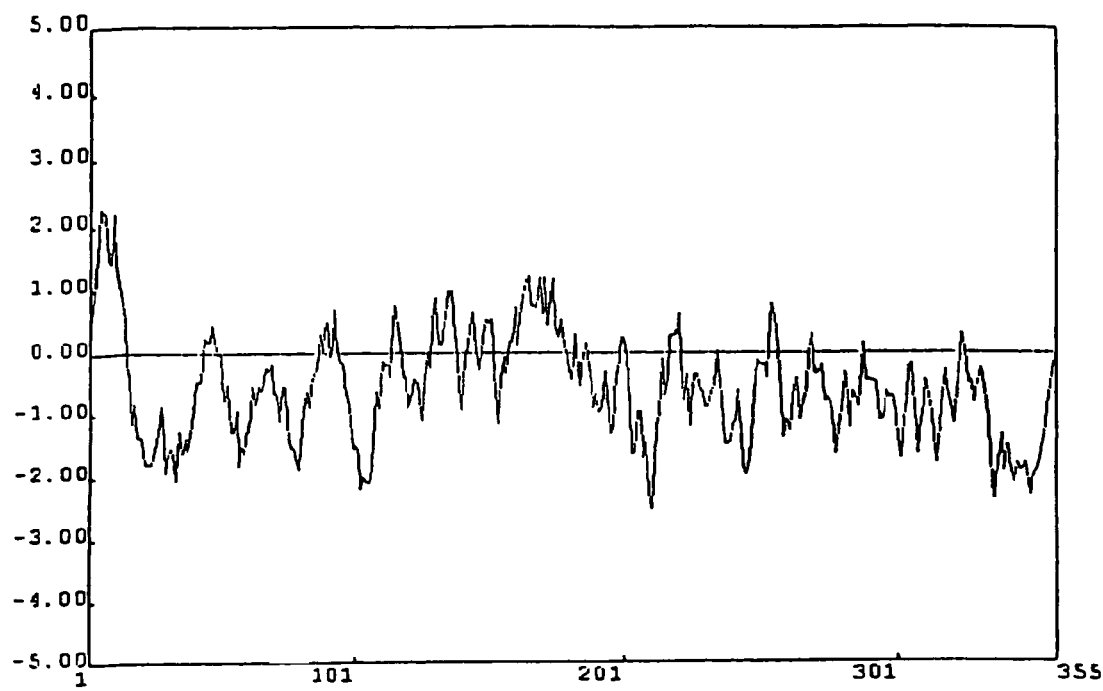
B) Prediction of the human VEGF-D signal peptide
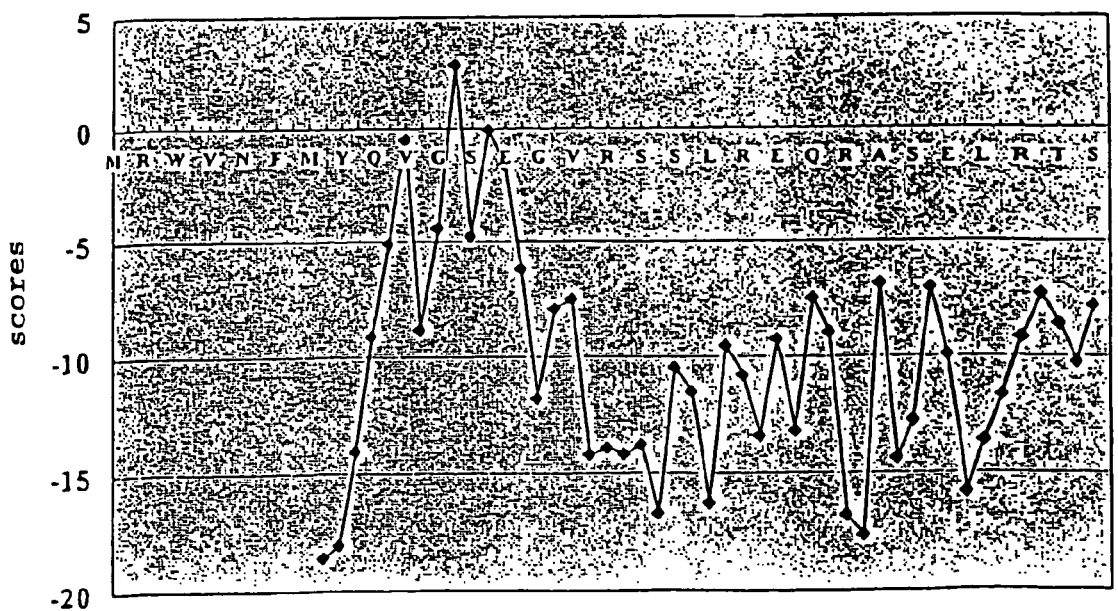

SEQUENCE LISTING

<160> NUMBER OF SEQ ID NOS: 34

<210> SEQ ID NO 1
<211> LENGTH: 354
<212> TYPE: PRT
<213> ORGANISM: Homo sapiens

<400> SEQUENCE: 1

Met Tyr Arg Glu Trp Val Val Asn Val Phe Met Met Leu Tyr Val
1               5                   10                  15

Gln Leu Val Gln Gly Ser Ser Asn Glu His Gly Pro Val Lys Arg Ser
            20                  25                  30

Ser Gln Ser Thr Leu Glu Arg Ser Glu Gln Gln Ile Arg Ala Ala Ser
        35                  40                  45

Ser Leu Glu Glu Leu Leu Arg Ile Thr His Ser Glu Asp Trp Lys Leu
    50                  55                  60

Trp Arg Cys Arg Leu Arg Leu Lys Ser Phe Thr Ser Met Asp Ser Arg
65                  70                  75                  80

Ser Ala Ser His Arg Ser Thr Arg Phe Ala Ala Thr Phe Tyr Asp Ile
                85                  90                  95

Glu Thr Leu Lys Val Ile Asp Glu Gly Trp Gln Arg Thr Gln Cys Ser
            100                 105                 110

Pro Arg Glu Thr Cys Val Glu Val Ala Ser Glu Leu Gly Lys Ser Thr
        115                 120                 125

Asn Thr Phe Phe Lys Pro Pro Cys Val Asn Val Phe Arg Cys Gly Gly
    130                 135                 140

Cys Cys Asn Glu Glu Ser Leu Ile Cys Met Asn Thr Ser Thr Ser Tyr
145                 150                 155                 160

Ile Ser Lys Gln Leu Phe Glu Ile Ser Val Pro Leu Thr Ser Val Pro
                165                 170                 175

Glu Leu Val Pro Val Lys Val Ala Asn His Thr Gly Cys Lys Cys Leu
            180                 185                 190

Pro Thr Ala Pro Arg His Pro Tyr Ser Ile Ile Arg Arg Ser Ile Gln
        195                 200                 205

Ile Pro Glu Glu Asp Arg Cys Ser His Ser Lys Lys Leu Cys Pro Ile
    210                 215                 220

Asp Met Leu Trp Asp Ser Asn Lys Cys Lys Cys Val Leu Gln Glu Glu
225                 230                 235                 240

Asn Pro Leu Ala Gly Thr Glu Asp His Ser His Leu Gln Glu Pro Ala
                245                 250                 255

Leu Cys Gly Pro His Met Met Phe Asp Glu Asp Arg Cys Glu Cys Val
            260                 265                 270

Cys Lys Thr Pro Cys Pro Lys Asp Leu Ile Gln His Pro Lys Asn Cys
        275                 280                 285

Ser Cys Phe Glu Cys Lys Glu Ser Leu Glu Thr Cys Cys Gln Lys His
    290                 295                 300

Lys Leu Phe His Pro Asp Thr Cys Ser Cys Glu Asp Arg Cys Pro Phe
305                 310                 315                 320

His Thr Arg Pro Cys Ala Ser Gly Lys Thr Ala Cys Ala Lys His Cys
                325                 330                 335

Arg Phe Pro Lys Glu Lys Arg Ala Ala Gln Gly Pro His Ser Arg Lys
            340                 345                 350

Asn Pro

-continued

```
<210> SEQ ID NO 2
<211> LENGTH: 2004
<212> TYPE: DNA
<213> ORGANISM: Homo sapiens
<220> FEATURE:
<221> NAME/KEY: CDS
<222> LOCATION: (403)...(1464)

<400> SEQUENCE: 2
ccagctttct gtarctgtaa gcattggtgg ccacaccacc tccttacaaa gcaactagaa      60
cctgcggcat acattggaga gattttttta attttctgga caygaagtaa atttagagtg     120
ctttcyaatt tcaggtagaa gacatgtcca ccttctgatt attttggag aacattttga      180 tttttttcat ctctctctcc ccaccccctaa gattgtgcaa aaaaagcgta ccttgcctaa    240
ttgaaataat ttcattggat tttgatcaga actgatcatt tggttttctg tgtgaagttt     300
tgaggtttca aactttcctt ctggagaatg ccttttgaaa caattttctc tagctgcctg     360
atgtcaactg cttagtaatc agtggatatt gaaatattca aa atg tac aga gag        414
                                                Met Tyr Arg Glu
                                                 1 tgg gta gtg gtg aat gtt ttc atg atg ttg tac gtc cag ctg gtg cag       462
Trp Val Val Val Asn Val Phe Met Met Leu Tyr Val Gln Leu Val Gln
  5              10                 15                  20 ggc tcc agt aat gaa cat gga cca gtg aag cga tca tct cag tcc aca       510
Gly Ser Ser Asn Glu His Gly Pro Val Lys Arg Ser Ser Gln Ser Thr
         25                 30                  35 ttg gaa cga tct gaa cag cag atc agg gct gct tct agt ttg gag gaa       558
Leu Glu Arg Ser Glu Gln Gln Ile Arg Ala Ala Ser Ser Leu Glu Glu
     40                  45                  50 cta ctt cga att act cac tct gag gac tgg aag ctg tgg aga tgc agg       606
Leu Leu Arg Ile Thr His Ser Glu Asp Trp Lys Leu Trp Arg Cys Arg
 55                  60                  65 ctg agg ctc aaa agt ttt acc agt atg gac tct cgc tca gca tcc cat       654
Leu Arg Leu Lys Ser Phe Thr Ser Met Asp Ser Arg Ser Ala Ser His
     70                  75                  80 cgg tcc act agg ttt gcg gca act ttc tat gac att gaa aca cta aaa       702
Arg Ser Thr Arg Phe Ala Ala Thr Phe Tyr Asp Ile Glu Thr Leu Lys
 85                  90                  95                 100 gtt ata gat gaa gaa tgg caa aga act cag tgc agc cct aga gaa acg       750
Val Ile Asp Glu Glu Trp Gln Arg Thr Gln Cys Ser Pro Arg Glu Thr
                105                 110                 115 tgc gtg gag gtg gcc agt gag ctg ggg aag agt acc aac aca ttc ttc       798
Cys Val Glu Val Ala Ser Glu Leu Gly Lys Ser Thr Asn Thr Phe Phe
            120                 125                 130 aag ccc cct tgt gtg aac gtg ttc cga tgt ggt ggc tgt tgc aat gaa       846
Lys Pro Pro Cys Val Asn Val Phe Arg Cys Gly Gly Cys Cys Asn Glu
        135                 140                 145 gag agc ctt atc tgt atg aac acc agc acc tcg tac att tcc aaa cag       894
Glu Ser Leu Ile Cys Met Asn Thr Ser Thr Ser Tyr Ile Ser Lys Gln
    150                 155                 160 ctc ttt gag ata tca gtg cct ttg aca tca gta cct gaa tta gtg cct       942
Leu Phe Glu Ile Ser Val Pro Leu Thr Ser Val Pro Glu Leu Val Pro
165                 170                 175                 180 gtt aaa gtt gcc aat cat aca ggt tgt aag tgc ttg cca aca gcc ccc       990
Val Lys Val Ala Asn His Thr Gly Cys Lys Cys Leu Pro Thr Ala Pro
                185                 190                 195 cgc cat cca tac tca att atc aga aga tcc atc cag atc cct gaa gaa      1038
Arg His Pro Tyr Ser Ile Ile Arg Arg Ser Ile Gln Ile Pro Glu Glu
            200                 205                 210
```

```
gat cgc tgt tcc cat tcc aag aaa ctc tgt cct att gac atg cta tgg      1086
Asp Arg Cys Ser His Ser Lys Lys Leu Cys Pro Ile Asp Met Leu Trp
        215                 220                 225 gat agc aac aaa tgt aaa tgt gtt ttg cag gag gaa aat cca ctt gct      1134
Asp Ser Asn Lys Cys Lys Cys Val Leu Gln Glu Glu Asn Pro Leu Ala
    230                 235                 240 gga aca gaa gac cac tct cat ctc cag gaa cca gct ctc tgt ggg cca      1182
Gly Thr Glu Asp His Ser His Leu Gln Glu Pro Ala Leu Cys Gly Pro
245                 250                 255                 260 cac atg atg ttt gac gaa gat cgt tgc gag tgt gtc tgt aaa aca cca      1230
His Met Met Phe Asp Glu Asp Arg Cys Glu Cys Val Cys Lys Thr Pro
                265                 270                 275 tgt ccc aaa gat cta atc cag cac ccc aaa aac tgc agt tgc ttt gag      1278
Cys Pro Lys Asp Leu Ile Gln His Pro Lys Asn Cys Ser Cys Phe Glu
            280                 285                 290 tgc aaa gaa agt ctg gag acc tgc tgc cag aag cac aag cta ttt cac      1326
Cys Lys Glu Ser Leu Glu Thr Cys Cys Gln Lys His Lys Leu Phe His
        295                 300                 305 cca gac acc tgc agc tgt gag gac aga tgc ccc ttt cat acc aga cca      1374
Pro Asp Thr Cys Ser Cys Glu Asp Arg Cys Pro Phe His Thr Arg Pro
    310                 315                 320 tgt gca agt ggc aaa aca gca tgt gca aag cat tgc cgc ttt cca aag      1422
Cys Ala Ser Gly Lys Thr Ala Cys Ala Lys His Cys Arg Phe Pro Lys
325                 330                 335                 340 gag aaa agg gct gcc cag ggg ccc cac agc cga aag aat cct              1464
Glu Lys Arg Ala Ala Gln Gly Pro His Ser Arg Lys Asn Pro
                345                 350 tgattcagcg ttccaagttc cccatccctg tcattttaa cagcatgctg ctttgccaag     1524
ttgctgtcac tgttttttc ccaggtgtta aaaaaaaat ccattttaca cagcaccaca     1584
gtgaatccag accaaccttc cattcacacc agctaaggag tccctggttc attgatggat   1644
gtcttctagc tgcagatgcc tctgcgcacc aaggaatgga gaggaggga cccatgtaat    1704 cctttgtt agttttgttt ttgttttttg gtgaatgaga aaggtgtgct ggtcatggaa     1764
tggcaggtgt catatgactg attactcaga gcagatgagg aaaactgtag tctctgagtc   1824
ctttgctaat cgcaactctt gtgaattatt ctgattcttt tttatgcaga atttgattcg   1884
tatgatcagt actgactttc tgattactgt ccagcttata gtcttccagt ttaatgaact   1944
accatctgat gtttcatatt taagtgtatt taaagaaaat aaacaccatt attcaagtct   2004

<210> SEQ ID NO 3
<211> LENGTH: 16
<212> TYPE: PRT
<213> ORGANISM: Homo sapiens

<400> SEQUENCE: 3

Cys Gly Pro Asn Lys Glu Leu Asp Glu Asn Thr Cys Gln Cys Val Cys
1               5                   10                  15

<210> SEQ ID NO 4
<211> LENGTH: 27
<212> TYPE: DNA
<213> ORGANISM: Artificial Sequence
<220> FEATURE:
<223> OTHER INFORMATION: Synthetic DNA

<400> SEQUENCE: 4
agggatgggg aacttggaac gctgaat                                        27
```

<210> SEQ ID NO 5
<211> LENGTH: 27
<212> TYPE: DNA
<213> ORGANISM: Artificial Sequence
<220> FEATURE:
<223> OTHER INFORMATION: Synthetic DNA

<400> SEQUENCE: 5
gatctaatcc agcaccccaa aaactgc                27

<210> SEQ ID NO 6
<211> LENGTH: 27
<212> TYPE: DNA
<213> ORGANISM: Artificial Sequence
<220> FEATURE:
<223> OTHER INFORMATION: Synthetic DNA

<400> SEQUENCE: 6
ccatcctaat acgactcact atagggc                27

<210> SEQ ID NO 7
<211> LENGTH: 33
<212> TYPE: DNA
<213> ORGANISM: Artificial Sequence
<220> FEATURE:
<223> OTHER INFORMATION: Synthetic DNA

<400> SEQUENCE: 7
ctggttcggc ccagaacttg gaacgctgaa tca             33

<210> SEQ ID NO 8
<211> LENGTH: 32
<212> TYPE: DNA
<213> ORGANISM: Artificial Sequence
<220> FEATURE:
<223> OTHER INFORMATION: Synthetic DNA

<400> SEQUENCE: 8
ctcgctcgcc cactaatacg actcactata gg              32

<210> SEQ ID NO 9
<211> LENGTH: 20
<212> TYPE: DNA
<213> ORGANISM: Artificial Sequence
<220> FEATURE:
<223> OTHER INFORMATION: Synthetic DNA

<400> SEQUENCE: 9
aattaaccct cactaaaggg                       20

<210> SEQ ID NO 10
<211> LENGTH: 22
<212> TYPE: DNA
<213> ORGANISM: Artificial Sequence
<220> FEATURE:
<223> OTHER INFORMATION: Synthetic DNA

<400> SEQUENCE: 10
ccagggtttt cccagtcacg ac                    22

<210> SEQ ID NO 11
<211> LENGTH: 23
<212> TYPE: DNA
<213> ORGANISM: Artificial Sequence
<220> FEATURE:
<223> OTHER INFORMATION: Synthetic DNA

```
<400> SEQUENCE: 11
actcactata gggctcgagc ggc                                         23

<210> SEQ ID NO 12
<211> LENGTH: 17
<212> TYPE: DNA
<213> ORGANISM: Artificial Sequence
<220> FEATURE:
<223> OTHER INFORMATION: Synthetic DNA

<400> SEQUENCE: 12
aagtctggag acctgct                                                17

<210> SEQ ID NO 13
<211> LENGTH: 17
<212> TYPE: DNA
<213> ORGANISM: Artificial Sequence
<220> FEATURE:
<223> OTHER INFORMATION: Synthetic DNA

<400> SEQUENCE: 13
cagcaggtct ccagact                                                17

<210> SEQ ID NO 14
<211> LENGTH: 17
<212> TYPE: DNA
<213> ORGANISM: Artificial Sequence
<220> FEATURE:
<223> OTHER INFORMATION: Synthetic DNA

<400> SEQUENCE: 14
cgcacccaag gaatgga                                                17

<210> SEQ ID NO 15
<211> LENGTH: 18
<212> TYPE: DNA
<213> ORGANISM: Artificial Sequence
<220> FEATURE:
<223> OTHER INFORMATION: Synthetic DNA

<400> SEQUENCE: 15
tgacacctgg ccattcca                                               18

<210> SEQ ID NO 16
<211> LENGTH: 18
<212> TYPE: DNA
<213> ORGANISM: Artificial Sequence
<220> FEATURE:
<223> OTHER INFORMATION: Synthetic DNA

<400> SEQUENCE: 16
catcagatgg tagttcat                                               18

<210> SEQ ID NO 17
<211> LENGTH: 20
<212> TYPE: DNA
<213> ORGANISM: Artificial Sequence
<220> FEATURE:
<223> OTHER INFORMATION: Synthetic DNA

<400> SEQUENCE: 17
atgctgagcg agagtccata                                             20

<210> SEQ ID NO 18
<211> LENGTH: 20
```

```
<212> TYPE: DNA
<213> ORGANISM: Artificial Sequence
<220> FEATURE:
<223> OTHER INFORMATION: Synthetic DNA

<400> SEQUENCE: 18
cactaggttt gcggcaactt                                                      20

<210> SEQ ID NO 19
<211> LENGTH: 20
<212> TYPE: DNA
<213> ORGANISM: Artificial Sequence
<220> FEATURE:
<223> OTHER INFORMATION: Synthetic DNA

<400> SEQUENCE: 19
gctgttggca agcacttaca                                                      20

<210> SEQ ID NO 20
<211> LENGTH: 20
<212> TYPE: DNA
<213> ORGANISM: Artificial Sequence
<220> FEATURE:
<223> OTHER INFORMATION: Synthetic DNA

<400> SEQUENCE: 20
gatccatcca gatccctgaa                                                      20

<210> SEQ ID NO 21
<211> LENGTH: 19
<212> TYPE: DNA
<213> ORGANISM: Artificial Sequence
<220> FEATURE:
<223> OTHER INFORMATION: Synthetic DNA

<400> SEQUENCE: 21
cagatcaggg ctgcttcta                                                       19

<210> SEQ ID NO 22
<211> LENGTH: 32
<212> TYPE: DNA
<213> ORGANISM: Artificial Sequence
<220> FEATURE:
<223> OTHER INFORMATION: Synthetic DNA

<400> SEQUENCE: 22
tccagatctt ttgcggcaac tttctatgac at                                        32

<210> SEQ ID NO 23
<211> LENGTH: 33
<212> TYPE: DNA
<213> ORGANISM: Artificial Sequence
<220> FEATURE:
<223> OTHER INFORMATION: Synthetic DNA

<400> SEQUENCE: 23
caggtcgact caaacaggca ctaattcagg tac                                       33

<210> SEQ ID NO 24
<211> LENGTH: 1581
<212> TYPE: DNA
<213> ORGANISM: Mus musculus
<220> FEATURE:
<221> NAME/KEY: CDS
<222> LOCATION: (96)...(1169)
<220> FEATURE:
<221> NAME/KEY: misc_feature
```

<222> LOCATION: (1)...(1581)
<223> OTHER INFORMATION: n = A,T,C or G

<400> SEQUENCE: 24

```
ttccgggctt tgctggagaa tgccttttgc aacactttc agtagctgcc tggaaacaac           60
tgcttagtca tcggtagaca tttaaaatat tcaaa atg tat gga gaa tgg gga            113
                                      Met Tyr Gly Glu Trp Gly
                                        1               5 atg ggg aat atc ctc atg atg ttc cat gtg tac ttg gtg cag ggc ttc           161
Met Gly Asn Ile Leu Met Met Phe His Val Tyr Leu Val Gln Gly Phe
            10                  15                  20 agg agc gaa cat gga cca gtg aag gat ttt tct ttt gag cga tca tcc           209
Arg Ser Glu His Gly Pro Val Lys Asp Phe Ser Phe Glu Arg Ser Ser
        25                  30                  35 cgg tcc atg ttg gaa cga tct gaa caa cag atc cga gca gct tct agt           257
Arg Ser Met Leu Glu Arg Ser Glu Gln Gln Ile Arg Ala Ala Ser Ser
    40                  45                  50 ttg gag gag ttg ctg caa atc gcg cac tct gag gac tgg aag ctg tgg           305
Leu Glu Glu Leu Leu Gln Ile Ala His Ser Glu Asp Trp Lys Leu Trp
55                  60                  65                  70 cga tgc cgg ttg aag ctc aaa agt ctt gcc agt atg gac tca cgc tca           353
Arg Cys Arg Leu Lys Leu Lys Ser Leu Ala Ser Met Asp Ser Arg Ser
                75                  80                  85 gca tcc cat cgc tcc acc aga ttt gcg gca act ttc tat gac act gaa           401
Ala Ser His Arg Ser Thr Arg Phe Ala Ala Thr Phe Tyr Asp Thr Glu
            90                  95                 100 aca cta aaa gtt ata gat gaa gaa tgg cag agg acc caa tgc agc cct           449
Thr Leu Lys Val Ile Asp Glu Glu Trp Gln Arg Thr Gln Cys Ser Pro
        105                 110                 115 aga gag aca tgc gta gaa gtc gcc agt gag ctg ggg aag aca acc aac           497
Arg Glu Thr Cys Val Glu Val Ala Ser Glu Leu Gly Lys Thr Thr Asn
    120                 125                 130 aca ttc ttc aag ccc ccc tgt gta aat gtc ttc cgg tgt gga ggc tgc           545
Thr Phe Phe Lys Pro Pro Cys Val Asn Val Phe Arg Cys Gly Gly Cys
135                 140                 145                 150 tgc aac gaa gag ggt gtg atg tgt atg aac aca agc acc tcc tac atc           593
Cys Asn Glu Glu Gly Val Met Cys Met Asn Thr Ser Thr Ser Tyr Ile
                155                 160                 165 tcc aaa cag ctc ttt gag ata tca gtg cct ctg aca tca gtg ccc gag           641
Ser Lys Gln Leu Phe Glu Ile Ser Val Pro Leu Thr Ser Val Pro Glu
            170                 175                 180 tta gtg cct gtt aaa att gcc aac cat acg ggt tgt aag tgc ttg ccc           689
Leu Val Pro Val Lys Ile Ala Asn His Thr Gly Cys Lys Cys Leu Pro
        185                 190                 195 acg ggc ccc cgc cat cct tac tca att atc aga aga tcc att cag acc           737
Thr Gly Pro Arg His Pro Tyr Ser Ile Ile Arg Arg Ser Ile Gln Thr
    200                 205                 210 cca gaa gaa gat gaa tgt cct cat tcc aag aaa ctc tgt cct att gac           785
Pro Glu Glu Asp Glu Cys Pro His Ser Lys Lys Leu Cys Pro Ile Asp
215                 220                 225                 230 atg ctg tgg gat aac acc aaa tgt aaa tgt gtt ttg caa gac gag act           833
Met Leu Trp Asp Asn Thr Lys Cys Lys Cys Val Leu Gln Asp Glu Thr
                235                 240                 245 cca ctg cct ggg aca gaa gac cac tct tac ctc cag gaa ccc act ctc           881
Pro Leu Pro Gly Thr Glu Asp His Ser Tyr Leu Gln Glu Pro Thr Leu
            250                 255                 260 tgt gga ccg cac atg acg ttt gat gaa gat cgc tgt gag tgc gtc tgt           929
Cys Gly Pro His Met Thr Phe Asp Glu Asp Arg Cys Glu Cys Val Cys
        265                 270                 275
```

```
aaa gca cca tgt ccg gga gat ctc att cag cac ccg gaa aac tgc agt      977
Lys Ala Pro Cys Pro Gly Asp Leu Ile Gln His Pro Glu Asn Cys Ser
    280             285                 290 tgc ttt gag tgc aaa gaa agt ctg gag agc tgc tgc caa aag cac aag     1025
Cys Phe Glu Cys Lys Glu Ser Leu Glu Ser Cys Cys Gln Lys His Lys
295             300                 305                     310 att ttt cac cca gac acc tgc agc tgt gag gac aga tgt cct ttt cac     1073
Ile Phe His Pro Asp Thr Cys Ser Cys Glu Asp Arg Cys Pro Phe His
                315                 320                 325 acc aga aca tgt gca agt aga aag cca gcc tgt gga aag cac tgg cgc     1121
Thr Arg Thr Cys Ala Ser Arg Lys Pro Ala Cys Gly Lys His Trp Arg
            330                 335                 340 ttt cca aag gag aca agg gcc cag gga ctc tac agc cag gag aac cct     1169
Phe Pro Lys Glu Thr Arg Ala Gln Gly Leu Tyr Ser Gln Glu Asn Pro
        345                 350                 355 tgattcaact tcctttcaag tcccccatc tctgtcattt taaacagctc actgctttgt    1229
caagttgctg tcactgttgc ccactacccc tgcccccccc cccccccgcc tccaggtgtt    1289
agaaaagttg atttgaccta gtgtcatggt aaagccacat ttccatgcaa tggcggctag    1349
gtgattcccc agttcactga caaatgactt gtagcttcaa atgtctttgc gccatcanca    1409
ctcaaaaagg aaggggtctg aagaacccct tgtttgataa ataaaaacag gtgcctgaaa    1469
caaaatatta ggtgccactc gattgggtcc ctcgggctgg ccaaattcca agggcaatgc    1529
tcctgaattt attgtgcccc ttccttaatg cggaatttcc ttttgtttga tt             1581

<210> SEQ ID NO 25
<211> LENGTH: 1491
<212> TYPE: DNA
<213> ORGANISM: Rat rattus
<220> FEATURE:
<221> NAME/KEY: CDS
<222> LOCATION: (270)...(1247)

<400> SEQUENCE: 25
gccacctctt gattatttgt gcagcgggaa actttgaaat agttttcatc tctttctccc     60
atactaagat tgtgtgtggc cgtgggggag tccttgacta actcaagtca tttcattgga   120
ttttgattac aactgatcat gtgatatttt tttccatgta aagttttggg gcttcaaact   180
ttgcttctgg agaatgccct ttgcaacact tttcagtagc tgcctggaaa caactgctta   240
gccatcagtg gacatttgaa atattcaaa atg tat gga gag tgg gcc gca gtg     293
                                 Met Tyr Gly Glu Trp Ala Ala Val
                                   1               5 aat att ctc atg atg tcc tat gtg tac ctg gtg cag ggc ttc agt att      341
Asn Ile Leu Met Met Ser Tyr Val Tyr Leu Val Gln Gly Phe Ser Ile
        10                  15                  20 gaa cac cga gca gtg aag gat gtt tct ctt gag cga tca tcc cgg tct      389
Glu His Arg Ala Val Lys Asp Val Ser Leu Glu Arg Ser Ser Arg Ser
 25                  30                  35                  40 gtg ttg gaa cgt tct gaa caa cag atc cgc gcg gct tct act ttg gaa      437
Val Leu Glu Arg Ser Glu Gln Gln Ile Arg Ala Ala Ser Thr Leu Glu
                45                  50                  55 gag ttg ctg caa gtc gca cac tct gag gac tgg aag ctg tgg cgg tgc      485
Glu Leu Leu Gln Val Ala His Ser Glu Asp Trp Lys Leu Trp Arg Cys
            60                  65                  70 cgg ttg aag ctt aaa agt ctt gcc aat gtg gac tcg cgc tca aca tcc      533
Arg Leu Lys Leu Lys Ser Leu Ala Asn Val Asp Ser Arg Ser Thr Ser
        75                  80                  85 cat cgc tcc acc aga ttt gcg gca act ttc tat gat act gaa aca cta      581
His Arg Ser Thr Arg Phe Ala Ala Thr Phe Tyr Asp Thr Glu Thr Leu
```

```
                90              95              100
aaa gtt ata gat gaa gaa tgg cag agg acc caa tgc agc cct aga gag    629
Lys Val Ile Asp Glu Glu Trp Gln Arg Thr Gln Cys Ser Pro Arg Glu
105                 110                 115                 120 aca tgc gta gaa gtc gcc agt gag ctg ggg aag aca acc aac aca ttt    677
Thr Cys Val Glu Val Ala Ser Glu Leu Gly Lys Thr Thr Asn Thr Phe
                125                 130                 135 ttc aag ccc cct tgt gta aat gtc ttc cgg tgt gga gga tgc tgc aat    725
Phe Lys Pro Pro Cys Val Asn Val Phe Arg Cys Gly Gly Cys Cys Asn
            140                 145                 150 gaa gag agc gtg atg tgt atg aac aca agc acc tcc tac atc tcc aaa    773
Glu Glu Ser Val Met Cys Met Asn Thr Ser Thr Ser Tyr Ile Ser Lys
        155                 160                 165 cag ctc ttt gag ata tca gtg cct ctg aca tca gtg ccc gag tta gtg    821
Gln Leu Phe Glu Ile Ser Val Pro Leu Thr Ser Val Pro Glu Leu Val
    170                 175                 180 cct gtt aaa att gcc aac cat acg ggt tgt aag tgt ttg ccc acg ggc    869
Pro Val Lys Ile Ala Asn His Thr Gly Cys Lys Cys Leu Pro Thr Gly
185                 190                 195                 200 ccc cgg cat cct tat tca att atc aga aga tcc att cag atc cca gaa    917
Pro Arg His Pro Tyr Ser Ile Ile Arg Arg Ser Ile Gln Ile Pro Glu
                205                 210                 215 gaa gat caa tgt cct cat tcc aag aaa ctc tgt cct gtt gac atg ctg    965
Glu Asp Gln Cys Pro His Ser Lys Lys Leu Cys Pro Val Asp Met Leu
            220                 225                 230 tgg gat aac acc aaa tgt aaa tgt gtt tta caa gat gag aat cca ctg    1013
Trp Asp Asn Thr Lys Cys Lys Cys Val Leu Gln Asp Glu Asn Pro Leu
        235                 240                 245 cct ggg aca gaa gac cac tct tac ctc cag gaa ccc gct ctc tgt gga    1061
Pro Gly Thr Glu Asp His Ser Tyr Leu Gln Glu Pro Ala Leu Cys Gly
    250                 255                 260 cca cac atg atg ttt gat gaa gat cgc tgc gag tgt gtc tgt aaa gca    1109
Pro His Met Met Phe Asp Glu Asp Arg Cys Glu Cys Val Cys Lys Ala
265                 270                 275                 280 cca tgt cct gga gat ctc att cag cac ccg gaa aac tgc agt tgc ttt    1157
Pro Cys Pro Gly Asp Leu Ile Gln His Pro Glu Asn Cys Ser Cys Phe
                285                 290                 295 gaa tgc aaa gaa agt ctg gaa agc tgt tgc caa aag cac aag atg ttt    1205
Glu Cys Lys Glu Ser Leu Glu Ser Cys Cys Gln Lys His Lys Met Phe
            300                 305                 310 cac cct gac acc tgc aga tca atg gtc ttt tca ctg tcc cct                1247
His Pro Asp Thr Cys Arg Ser Met Val Phe Ser Leu Ser Pro
        315                 320                 325 taatttggtt tactggtgac atttaaagga catactaacc tgatttattg gggctctttt    1307
ctctcagggc ccaagcacac tcttaaagga acacagacgt tggcctcta agaaatacat     1367 ggaagtatta tagagtgatg attaaattgt cttcttgttt caaacagggt ctcatgatta    1427
cagacccgta ttgccatgcc tgccgtcatg ctatcatgag cggaaaagaa tcactggcat    1487
ttaa                                                                  1491

<210> SEQ ID NO 26
<211> LENGTH: 20
<212> TYPE: DNA
<213> ORGANISM: Artificial Sequence
<220> FEATURE:
<223> OTHER INFORMATION: Synthetic DNA

<400> SEQUENCE: 26
gctgcgagtg tgtctgtaaa                                                  20
```

<210> SEQ ID NO 27
<211> LENGTH: 25
<212> TYPE: DNA
<213> ORGANISM: Artificial Sequence
<220> FEATURE:
<223> OTHER INFORMATION: Synthetic DNA

<400> SEQUENCE: 27
gggtagtggg caacagtgac agcaa					25

<210> SEQ ID NO 28
<211> LENGTH: 104
<212> TYPE: PRT
<213> ORGANISM: Homo sapiens

<400> SEQUENCE: 28

His Leu Gln Glu Pro Ala Leu Cys Gly Pro His Met Met Phe Asp Glu
1               5                   10                  15

Asp Arg Cys Glu Cys Val Cys Lys Thr Pro Cys Pro Lys Asp Leu Ile
            20                  25                  30

Gln His Pro Lys Asn Cys Ser Cys Phe Glu Cys Lys Glu Ser Leu Glu
        35                  40                  45

Thr Cys Cys Gln Lys His Lys Leu Phe His Pro Asp Thr Cys Ser Cys
    50                  55                  60

Glu Asp Arg Cys Pro Phe His Thr Arg Pro Cys Ala Ser Gly Lys Thr
65                  70                  75                  80

Ala Cys Ala Lys His Cys Arg Phe Pro Lys Glu Lys Arg Ala Ala Gln
                85                  90                  95

Gly Pro His Ser Arg Lys Asn Pro
            100

<210> SEQ ID NO 29
<211> LENGTH: 419
<212> TYPE: PRT
<213> ORGANISM: Homo sapiens

<400> SEQUENCE: 29

Met His Leu Leu Gly Phe Phe Ser Val Ala Cys Ser Leu Leu Ala Ala
1               5                   10                  15

Ala Leu Leu Pro Gly Pro Arg Glu Ala Pro Ala Ala Ala Ala Ala Phe
            20                  25                  30

Glu Ser Gly Leu Asp Leu Ser Asp Ala Glu Pro Asp Ala Gly Glu Ala
        35                  40                  45

Thr Ala Tyr Ala Ser Lys Asp Leu Glu Phe Gln Leu Arg Ser Val Ser
    50                  55                  60

Ser Val Asp Glu Leu Met Thr Val Leu Tyr Pro Glu Tyr Trp Lys Met
65                  70                  75                  80

Tyr Lys Cys Gln Leu Arg Lys Gly Gly Trp Gln His Asn Arg Glu Gln
                85                  90                  95

Ala Asn Leu Asn Ser Arg Thr Glu Glu Thr Ile Lys Phe Ala Ala Ala
            100                 105                 110

His Tyr Asn Thr Glu Ile Leu Lys Ser Ile Asp Asn Glu Trp Arg Lys
        115                 120                 125

Thr Gln Cys Met Pro Arg Glu Val Cys Ile Asp Val Gly Lys Glu Phe
    130                 135                 140

Gly Val Ala Thr Asn Thr Phe Phe Lys Pro Pro Cys Val Ser Val Tyr
145                 150                 155                 160

```
Arg Cys Gly Gly Cys Cys Asn Ser Glu Gly Leu Gln Cys Met Asn Thr
                165                 170                 175

Ser Thr Ser Tyr Leu Ser Lys Thr Leu Phe Glu Ile Thr Val Pro Leu
            180                 185                 190

Ser Gln Gly Pro Lys Pro Val Thr Ile Ser Phe Ala Asn His Thr Ser
        195                 200                 205

Cys Arg Cys Met Ser Lys Leu Asp Val Tyr Arg Gln Val His Ser Ile
    210                 215                 220

Ile Arg Arg Ser Leu Pro Ala Thr Leu Pro Gln Cys Gln Ala Ala Asn
225                 230                 235                 240

Lys Thr Cys Pro Thr Asn Tyr Met Trp Asn Asn His Ile Cys Arg Cys
                245                 250                 255

Leu Ala Gln Glu Asp Phe Met Phe Ser Asp Ala Gly Asp Asp Ser
            260                 265                 270

Thr Asp Gly Phe His Asp Ile Cys Gly Pro Asn Lys Glu Leu Asp Glu
            275                 280                 285

Glu Thr Cys Gln Cys Val Cys Arg Ala Gly Leu Arg Pro Ala Ser Cys
    290                 295                 300

Gly Pro His Lys Glu Leu Asp Arg Asn Ser Cys Gln Cys Val Cys Lys
305                 310                 315                 320

Asn Lys Leu Phe Pro Ser Gln Cys Gly Ala Asn Arg Glu Phe Asp Glu
                325                 330                 335

Asn Thr Cys Gln Cys Val Cys Lys Arg Thr Cys Pro Arg Asn Gln Pro
            340                 345                 350

Leu Asn Pro Gly Lys Cys Ala Cys Glu Cys Thr Glu Ser Pro Gln Lys
        355                 360                 365

Cys Leu Leu Lys Gly Lys Lys Phe His His Gln Thr Cys Ser Cys Tyr
    370                 375                 380

Arg Arg Pro Cys Thr Asn Arg Gln Lys Ala Cys Glu Pro Gly Phe Ser
385                 390                 395                 400

Tyr Ser Glu Glu Val Cys Arg Cys Val Pro Ser Tyr Trp Lys Arg Pro
                405                 410                 415

Gln Met Ser

<210> SEQ ID NO 30
<211> LENGTH: 211
<212> TYPE: PRT
<213> ORGANISM: Homo sapiens

<400> SEQUENCE: 30

Met Arg Thr Leu Ala Cys Leu Leu Leu Gly Cys Gly Tyr Leu Ala
 1               5                  10                  15

His Val Leu Ala Glu Glu Ala Glu Ile Pro Arg Glu Val Ile Glu Arg
                20                  25                  30

Leu Ala Arg Ser Gln Ile His Ser Ile Arg Asp Leu Gln Arg Leu Leu
            35                  40                  45

Glu Ile Asp Ser Val Gly Ser Glu Asp Ser Leu Asp Thr Ser Leu Arg
    50                  55                  60

Ala His Gly Val His Ala Thr Lys His Val Pro Phe Lys Arg Pro Leu
65                  70                  75                  80

Pro Ile Arg Arg Lys Arg Ser Ile Glu Glu Ala Val Pro Ala Val Cys
                85                  90                  95

Lys Thr Arg Thr Val Ile Tyr Glu Ile Pro Arg Ser Gln Val Asp Pro
            100                 105                 110
```

```
Thr Ser Ala Asn Phe Leu Ile Trp Pro Pro Cys Val Glu Val Lys Arg
        115                 120                 125

Cys Thr Gly Cys Cys Asn Thr Ser Val Lys Cys Gln Pro Ser Arg
        130                 135                 140

Val His His Arg Ser Val Lys Val Ala Lys Val Glu Tyr Val Arg Lys
145                 150                 155                 160

Lys Pro Lys Leu Lys Glu Val Gln Val Arg Leu Glu Glu His Leu Glu
                165                 170                 175

Cys Ala Cys Ala Thr Thr Ser Leu Asn Pro Asp Tyr Arg Glu Glu Asp
            180                 185                 190

Thr Gly Arg Pro Arg Glu Ser Gly Lys Lys Arg Lys Arg Leu
        195                 200                 205

Lys Pro Thr
    210

<210> SEQ ID NO 31
<211> LENGTH: 241
<212> TYPE: PRT
<213> ORGANISM: Homo sapiens

<400> SEQUENCE: 31

Met Asn Arg Cys Trp Ala Leu Phe Leu Ser Leu Cys Cys Tyr Leu Arg
1               5                   10                  15

Leu Val Ser Ala Glu Gly Asp Pro Ile Pro Glu Glu Leu Tyr Glu Met
                20                  25                  30

Leu Ser Asp His Ser Ile Arg Ser Phe Asp Asp Leu Gln Arg Leu Leu
            35                  40                  45

His Gly Asp Pro Gly Glu Glu Asp Gly Ala Glu Leu Asp Leu Asn Met
        50                  55                  60

Thr Arg Ser His Ser Gly Gly Glu Leu Glu Ser Leu Ala Arg Gly Arg
65                  70                  75                  80

Arg Ser Leu Gly Ser Leu Thr Ile Ala Glu Pro Ala Met Ile Ala Glu
                85                  90                  95

Cys Lys Thr Arg Thr Glu Val Phe Glu Ile Ser Arg Arg Leu Ile Asp
            100                 105                 110

Arg Thr Asn Ala Asn Phe Leu Val Trp Pro Pro Cys Val Glu Val Gln
        115                 120                 125

Arg Cys Ser Gly Cys Cys Asn Asn Arg Asn Val Gln Cys Arg Pro Thr
    130                 135                 140

Gln Val Gln Leu Arg Pro Val Gln Val Arg Lys Ile Glu Ile Val Arg
145                 150                 155                 160

Lys Lys Pro Ile Phe Lys Lys Ala Thr Val Thr Leu Glu Asp His Leu
                165                 170                 175

Ala Cys Lys Cys Glu Thr Val Ala Ala Ala Arg Pro Val Thr Arg Ser
            180                 185                 190

Pro Gly Gly Ser Gln Glu Gln Arg Ala Lys Thr Pro Gln Thr Arg Val
        195                 200                 205

Thr Ile Arg Thr Val Arg Val Arg Arg Pro Pro Lys Gly Lys His Arg
    210                 215                 220

Lys Phe Lys His Thr His Asp Lys Thr Ala Leu Lys Glu Thr Leu Gly
225                 230                 235                 240

Ala

<210> SEQ ID NO 32
```

<211> LENGTH: 170
<212> TYPE: PRT
<213> ORGANISM: Homo sapiens

<400> SEQUENCE: 32

Met Pro Val Met Arg Leu Phe Pro Cys Phe Leu Gln Leu Leu Ala Gly
1               5                   10                  15

Leu Ala Leu Pro Ala Val Pro Pro Gln Gln Trp Ala Leu Ser Ala Gly
            20                  25                  30

Asn Gly Ser Ser Glu Val Glu Val Pro Phe Gln Phe Val Trp Gly
        35                  40                  45

Arg Ser Tyr Cys Arg Ala Leu Glu Arg Leu Val Asp Val Val Ser Glu
    50                  55                  60

Tyr Pro Ser Glu Val Glu His Met Phe Ser Pro Ser Cys Val Ser Leu
65                  70                  75                  80

Leu Arg Cys Thr Gly Cys Cys Gly Asp Glu Asn Leu His Cys Val Pro
            85                  90                  95

Val Glu Thr Ala Asn Val Thr Met Gln Leu Leu Lys Ile Arg Ser Gly
            100                 105                 110

Asp Arg Pro Ser Tyr Val Glu Leu Thr Phe Ser Gln His Val Arg Cys
            115                 120                 125

Glu Cys Arg Pro Leu Arg Glu Lys Met Lys Pro Glu Arg Arg Arg Pro
130                 135                 140

Lys Gly Arg Gly Lys Arg Arg Glu Lys Gln Arg Pro Thr Asp Cys
145                 150                 155                 160

His Leu Cys Gly Asp Ala Val Pro Arg Arg
                165                 170

<210> SEQ ID NO 33
<211> LENGTH: 232
<212> TYPE: PRT
<213> ORGANISM: Homo sapiens

<400> SEQUENCE: 33

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
            85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
            115                 120                 125

Glu Cys Arg Pro Lys Lys Asp Arg Ala Arg Gln Glu Lys Lys Ser Val
130                 135                 140

Arg Gly Lys Gly Lys Gly Gln Lys Arg Lys Arg Lys Lys Ser Arg Tyr
145                 150                 155                 160

Lys Ser Trp Ser Val Tyr Val Gly Ala Arg Cys Cys Leu Met Pro Trp
                165                 170                 175

```
Ser Leu Pro Gly Pro His Pro Cys Gly Pro Cys Ser Glu Arg Arg Lys
            180                 185                 190

His Leu Phe Val Gln Asp Pro Gln Thr Cys Lys Cys Ser Cys Lys Asn
            195                 200                 205

Thr Asp Ser Arg Cys Lys Ala Arg Gln Leu Glu Leu Asn Glu Arg Thr
            210                 215                 220

Cys Arg Cys Asp Lys Pro Arg Arg
225             230

<210> SEQ ID NO 34
<211> LENGTH: 188
<212> TYPE: PRT
<213> ORGANISM: Homo sapiens

<400> SEQUENCE: 34

Met Ser Pro Leu Leu Arg Arg Leu Leu Leu Ala Ala Leu Leu Gln Leu
1               5                   10                  15

Ala Pro Ala Gln Ala Pro Val Ser Gln Pro Asp Ala Pro Gly His Gln
            20                  25                  30

Arg Lys Val Val Ser Trp Ile Asp Val Tyr Thr Arg Ala Thr Cys Gln
            35                  40                  45

Pro Arg Glu Val Val Val Pro Leu Thr Val Glu Leu Met Gly Thr Val
            50                  55                  60

Ala Lys Gln Leu Val Pro Ser Cys Val Thr Val Gln Arg Cys Gly Gly
65                  70                  75                  80

Cys Cys Pro Asp Asp Gly Leu Glu Cys Val Pro Thr Gly Gln His Gln
                85                  90                  95

Val Arg Met Gln Ile Leu Met Ile Arg Tyr Pro Ser Ser Gln Leu Gly
            100                 105                 110

Glu Met Ser Leu Glu Glu His Ser Gln Cys Glu Cys Arg Pro Lys Lys
            115                 120                 125

Lys Asp Ser Ala Val Lys Pro Asp Ser Pro Arg Pro Leu Cys Pro Arg
            130                 135                 140

Cys Thr Gln His His Gln Arg Pro Asp Pro Arg Thr Cys Arg Cys Arg
145                 150                 155                 160

Cys Arg Arg Arg Ser Phe Leu Arg Cys Gln Gly Arg Gly Leu Glu Leu
                165                 170                 175

Asn Pro Asp Thr Cys Arg Cys Arg Lys Leu Arg Arg
            180                 185
```

NUCLEIC ACID SEQUENCES ENCODING VEGF-LIKE FACTORS AND USES THEREOF

CROSS-REFERENCE TO RELATED APPLICATIONS

This application is a continuation of U.S. patent application Ser. No. 10/978,107, filed on Oct. 29, 2004, now abandoned., which, in turn, is a divisional of U.S. patent application Ser. No. 09/214,982, filed Jan. 14, 1999, now U.S. Pat. No. 6,828,426, which is the U.S. national stage application of International Application Number PCT/JP97/02456, filed Jul. 15, 1997, which, in turn, claims the benefit of Japanese Application Serial Number 8/185216, filed Jul. 15, 1996.

TECHNICAL FIELD

The present invention relates to a protein factor involved in angiogenesis in humans and falls in the field of genetic engineering.

BACKGROUND ART

The process of angiogenesis, in which endothelial cells existing in the inner wall of blood vessels of animals generate new blood vessels, is triggered by transduction of a specific signal. A variety of substances are reportedly involved in this signal transduction. The most notable substance among them is the vascular endothelial growth factor (VEGF). VEGF is a protein factor which was isolated and purified, and can increase the proliferation of endothelial cells and the permeability of blood vessels (Senger, D. R. et al., Science 219: 983-985 (1983); Ferrara, N. and Henzel, W. J., Biochem. Biophys. Res. Commun. 161: 851-858 (1989)). It has been reported that the human VEGF gene contains eight exons and produces four subtypes consisting of 121, 165, 189, or 206 amino acid residues, depending on the difference in splicing, which causes different secretion patterns (Houck, K. A. et al., Mol. Endocrinol. 5: 1806-1814 (1991)). -It has also been reported that there is a VEGF-specific receptor, flt-1, and that the binding of VEGF to flt-1 is. important for the signal transduction (Vries, C. D. et al., Science 255: 989-991 (1992)).

Placental growth factor (PlGF) and platelet-derived growth factor (PDGF) have thus far been isolated and are factors related to VEGF. These factors are found to promote proliferation activities of vascular endothelial cells (Maglione, D. et al., Proc. Natl. Acad. Sci. USA 88: 9267-9271 (1991); Betsholtz, C. et al., Nature 320: 695-699(1986)). Inaddition, VEGF-B (Olofsson, B. et al., Proc. Natl. Acad. Sci. USA 93: 2576-2581 (1996)) and VEGF-C (Lee, J. et al., Proc. Natl. Acad. Sci. USA 93: 1988-1992 (1996); Joukov, V. et al., EMBO J. 15, 290-299 (1996)) have recently been isolated.

These factors appear to constitute a family, and this may contain additional unknown factors.

It has been suggested that VEGF is involved in not only-vascular formation at the developmental stage but also in the pathological neovascularization associated with diabetes, rheumatoid arthritis, retinopathy, and the growth of solid tumors. Furthermore, in addition to its vascular endothelial cell growth-promoting effects listed above, VEGF's ability to increase vascular permeability was suggested to be involved in the edema formation resulting from various causes. Also, these VEGF family factors may act on not only the blood vessels but also the blood cells and the lymphatic vessels. They may thus play a role in the differentiation and proliferation of blood cells and the formation of lymphatic vessels. Consequently, the VEGF family factors are presently drawing extraordinary attention for developing useful, novel drugs.

DISCLOSURE OF THE INVENTION

An objective of the present invention is to isolate a novel protein belonging to the VEGF family and a gene encoding the protein. we searched for genes having homology to VEGF-C, which is a recently cloned VEGF family gene, against Expressed Sequence Tags (EST) and Sequence Tagged Sites (STS) in the GenBank database. As a result, we found an EST that was assumed to have homology to the C-terminal portion of VEGF-C. We then designed primers based on the sequence, and amplified and isolated the corresponding cDNA using the 5'RACE method and the 3'RACE method. The nucleotide sequence of the isolated cDNA was determined, and the deduced amino acid sequence therefrom revealed that the amino acid sequence had significant homology to that of VEGF-C. Based on the homology, we have assumed that the isolated human clone is a fourth member of the VEGF family (hereinafter designated as VEGF-D). We have also succeeded in expressing the protein encoded by the isolated human VEGF-D gene in E. coli cells, and have also purified and isolated it. Furthermore, we have succeeded in isolating the mouse and rat VEGF-D genes using the isolated human VEGF-D gene.

In particular, the present invention relates to a novel protein belonging to the VEGF family and a gene encoding the protein. More specifically it relates to (1) A protein shown by SEQ ID NO. 1 or having the amino acid sequence derived therefrom in which one or more amino acids are substituted, deleted, or added;

(2) A protein encoded by a DNA that hybridizes with the DNA shown by SEQ ID NO. 2;

(3) A DNA encoding the protein of (1);

(4) A DNA hybridizing with the DNA shown by SEQ ID NO. 2;

(5) A vector containing the DNA of (3) or (4);

(6) A transformant carrying the vector of (5);

(7) A method of producing the protein of (1) or (2), which comprises culturing the transformant of (6);

(8) An antibody binding to the protein of (1) or (2);

(9) A method of screening a compound binding to the protein of (1) or (2), which comprises a step of detecting the activity of the protein of (1) or (2) to bind to a test sample; and

(10) A compound binding to the protein of (1) or (2), wherein said compound has been isolated by the method of (9).

The protein of the present invention (VEGF-D) has significant homology to VEGF-C and can be considered to be a fourth factor of the VEGF family. Since the major function of VEGF is vascular formation at the developmental stage and VEGF is considered to be involved in the pathological neovascularization associated with diabetes, rheumatoid arthritis, retinopathy, and the growth of solid tumors, the protein of the present invention is thought to have similar functions.

A person skilled in the art could prepare functionally equivalent proteins through modifying VEGF-D of the present invention by adding, deleting, or substituting one or more of the amino acids of VEGF-D shown by SEQ ID NO. 1 using known methods. Modifications of the protein can also occur naturally in addition to the artificial modifications described above. These modified proteins are also included in the present invention. Known methods for adding, deleting, or substituting amino acids include the overlap extension polymerase chain reaction (OE-PCR) method (Gene, 1989, 77 (1): 51).

The DNA encoding VEGF-D of the present invention, shown by SEQ ID NO. 2, is useful for isolating DNAs encoding the proteins having similar functions to VEGF-D in other organisms. For example, a person skilled in the art could routinely isolate homologs of human VEGF-D of the present invention from other organisms by allowing the DNA shown by SEQ ID NO. 2, or part thereof, as a probe, to hybridize with the DNA derived from other organisms. The DNA that hybridizes with the DNA shown by SEQ ID NO. 2 is also included in the present invention. The other organisms include mice, rats, and rabbits.

The DNA encoding a protein that is functionally equivalent to VEGF-D usually has high homology to the DNA shown by SEQ ID NO. 2. The high homology used herein means at least 70% or higher, more preferably 80% or higher, and still more preferably 90% or higher of sequence homology.

An example of the hybridization conditions for isolating the DNA having high homology will be given below. Prehybridization is performed in ExpressHyb Solution at 68° C. for 30 minutes. The probe labeled with a radioisotope is denatured at 95° C. to 100° C. for 2 to 5 minutes and rapidly chilled on ice. The probe is added to a new ExpressHyb Solution. The blot is transferred to the solution containing the probe and allowed to hybridize under a temperature gradient of 68° C. to 55° C. for 2 hours. The blot is washed four times, for 10 minute each, with a 2×SSC solution containing 0.05% SDS at room temperature. The blot is then washed with a 0.1×SSC solution containing 0.1% SDS at 45° C. for 3 minutes. The blot is subjected to autoradiography.

An example of the hybridization conditions for isolating the DNA having very high homology will be given below. Prehybridization is performed in ExpressHyb Solution at 68° C. for 30 minutes. The probe labeled with a radioisotope is denatured at 95° C. to 100° C. for 2 to 5 minutes and rapidly chilled on ice. The probe is added into a new ExpressHyb Solution. The blot is transferred into the solution containing the probe, and allowed to hybridize at 68° C. for 1 hour. The blot was washed four times, for 10 minute each, with a 2×SSC solution containing 0.05% SDS at room temperature. The blot was then washed with a 0.1×SSC solution containing 0.1% SDS at 50° C. for 40 minutes, during which the solution was replaced once. The blot was then subjected to autoradiography.

Note that the hybridization condition can vary depending on the length of the probe (whether it is an oligomer or a probe with more than several hundred bases), the labeling method (whether the probe is radioisotopically labeled or non-radioisotopically labeled), and the type of the target gene to be cloned. A person skilled in the art would properly select the suitable hybridization conditions. In the present invention, it is especially desirable that the condition does not allow the probe to hybridize with the DNA encoding VEGF-C.

The DNA of the present invention is also used to produce VEGF-D of the present invention as a recombinant protein. Specifically, the recombinant protein can be produced in large quantity by incorporating the DNA encoding VEGF-D (for example, the DNA shown by SEQ ID NO. 2)into a suitable expression vector, introducing the resulting vector into a host, and culturing the transformant to allow the recombinant protein to be expressed.

The vector to be used for producing the recombinant protein is not particularly restricted. However, vectors such as PGEMEX-1 (Promega) or pEF-BOS (Nucleic Acids Res. 1990, 18(17): p.5322) are preferable. Suitable examples of the host into which the vector is introduced include E. coli cells, CHO. cells, and COS cells.

The VEGF-D protein expressed by the transformant can be purified by suitably combining purification treatments such as solubilization with a homogenizer or a sonicator, extraction by various buffers, solubilization or precipitation by acid or alkali, extraction or precipitation with organic solvents, salting out by ammonium sulfate and other agents, dialysis, ultrafiltration using membrane filters, gel filtration, ion exchange chromatography, reversed-phase chromatography, counter-current distribution. chromatography, high-performance liquid chromatography,-isoelectric focusing, gel electrophoresis, or affinity chromatography in which antibodies or receptors are immobilized.

Once the recombinant protein is obtained, antibodies against it can be prepared using known methods. The known methods include preparing polyclonal antibodies by immunizing rabbits, sheep, or other animals with the purified protein, and preparing monoclonal antibodies from the antibody-producing cells of immunized mice or rats. These antibodies will make it possible to quantify VEGF. Although the antibodies thus obtained can be used as they are, it will be more effective to use the humanized antibodies to reduce the immunogenicity. The methods of humanizing the antibodies include the CDR graft method and the method of directly producing a human antibody. In the CDR Graft method, the antibody gene is cloned from the monoclonal antibody-producing cells and its antigenic determinant portion is transplanted into an existing human antibody. In the method of directly producing a human antibody, a mouse whose immune system has been replaced by the human immune system is immunized, similar to ordinary monoclonal antibodies. The VEGF-D protein or its antibody thus obtained can be administered into the body by subcutaneous injection or a similar method.

A person skilled in the art could screen compounds that bind to the protein of the present invention by known methods.

For example, such compounds can be obtained by making a cDNA library on a phage vector (such as A gtll and ZAP) from the cells expected to express the protein that binds to the protein of the present invention (such as lung, small intestine, and heart cells of mammals), expressing the cDNAs on LB-agarose, fixing the expressed proteins onto a filter, preparing the purified protein of the present invention as a biotin-labeled or a fusion proteinwith the GSTprotein, and reacting this protein with the above filter. The desired compounds could then be detected by west western blotting using streptavidin or an anti-GST antibody (Skolnik, E. Y., Margolis, B., Mohammadi, M., Lowenstein, E., Fischer, R., Drepps, A., Ullrich, A., and Schlessinger, J. (1991) Cloning of P13 kinase-associated p85 utilizing a novel method for expression/cloning of target proteins for receptor tyrosine kinases, Cell 65: 83-90). Another method comprises the following steps. First, express the protein of.the present invention fused-withtheSRF bindingdomainortheGAL4 binding domain in yeast cells. Second, prepare a cDNA library which expresses cDNAs fused with the transcription activation domain of VP16 or GAL4 from the cells expected to express a protein that binds to the protein of the present invention. Third, introduce the cDNA into the above yeast cells. Fourth, isolate the library-derived cDNA from the positive clones. Finally, introduce the isolated cDNA into E. coli to allow it to be expressed. (When a protein that binds to the protein of the present invention is expressed in yeast cells, the reporter gene is activated and the positive clone can be detected.) This method can be performed using the two-hybrid system (MATCHMAKER Two-Hybrid System, Mammalian MATCHMAKER Two-Hybrid Assay Kit, or MATCHMAKER One-Hybrid System (all by Clontech) or the HybriZAP Two-Hybrid Vector System (Stratagene) (Dalton, S. and Treisman, R. (1992) Characterization of SAP-1, a protein recruited by serum response factor to the c-fos serum response element, Cell 68: 597-612). Alternatively, the binding proteins can be screened by preparing a cDNA library from the cells expected to express a substance, such as a receptor, which binds to the protein of the present invention (for example, vascular endothelial cells, bone marrow cells, or lymph duct cells)-, introducing it into such cells as COS, detecting the binding of the protein of the present invention by itself or labeled. with a radioisotope or a fluorescence, and cloning proteins that bind to the protein of the present invention (Yamasaki, K., Taga, T., Hirata, Y., Yawata, H., Kawanishi, Y., Seed, B., Taniguchi, T., Hirano, T., and Kishimoto, T. (1988) Cloning and expression of human interleukin-6 (BSF-2/IFN beta2) receptor, Science 241: 825-828, Fukunaga, R., Ishizaka-Ikeda, E., Seto, Y., and Nagata, S. (1990) Expressioncloning of a receptor for murine granulocyte colony-stimulating factor, Cell 61: 341-350). Still another method comprises applying the culture supernatant or the cellular extract of the cells expected to express a protein that binds to the protein of the present invention onto an affinity column to which the protein of the present invention has been immobilized, and purifying the proteins specifically bound to the column. In addition, a DNA encoding the protein that binds to the protein of the present invention can be obtained by determining the amino acid sequence of the binding protein, synthesizing oligonucleotides based on the sequence, and screening a cDNA library with the oligonucleotides as probes.

Furthermore, compounds that bind to the protein of the present invention can be screened by contacting compounds, a natural substance bank, or a random phage peptide display library with the immobilized protein of the present invention and detecting the molecules bound to the protein. These compounds can also be screened by high throughput screening utilizing combinatorial chemistry technology (Wrighton, N. C., Farrell, F. X., Chang, R., Kashyap, A. K., Barbone, F. P., Mulcahy, L. S., Johnson, D. L., Barrett, R. W., Jolliffe, L. K., and Dower, W. J., Small peptides as potent mimetics of the protein hormone erythropoietin, Science (United States) Jul. 26, 1996, 273: 458-464, Verdine, G. L., The combinatorial chemistry of nature, Nature (England) Nov. 7, 1996, 384: 11-13, Hogan, J.C. Jr. Directed combinatorial chemistry, Nature (England) Nov. 7, 1996, 384: 17-19).

VEGF-D of the present invention may be used for gene therapy by introducing the VEGF-D gene into the body of the patient with the VEGF-D deficiency, or expressing the gene in the body. An anti-sense DNA of the VEGF-D gene may also be used to inhibit the expression of the gene itself, thereby suppressing the pathological neovascularization.

Among the many available methods to introduce the VEGF-D gene or its antisense DNA into the body, the retrovirus method, the liposome method, the cationic liposome method, and the adenovirus method are preferable.

In order to express these genes in the body, the genes can be incorporated into a suitable vector and introduced into the body by the retrovirus method, the liposome method, the cationic liposome method, or the adenovirus method. Although the vectors to be used are not particularly limited, such vectors as pAdexlcw and pZIPneo are preferable.

The present invention may also be applied for diagnosing disorders caused by abnormalities of the VEGF-D gene, for example, by PCR to detect an abnormality of the nucleotide sequence of the VEGF-D gene.

Furthermore, according to the present invention, the VEGF-D protein or its agonists can be used to heal wounds, promote collateral vessel formation, and aid hematopoiesis by the hematopoietic stem cells, by taking advantage of the angiogenic effect of the VEGF-D protein. The antibodies against the VEGF-D protein or its antagonists can be used as the therapeutic agents for pathological neovascularization, lymphatic dysplasia, dyshematopoiesis, or edemas. arising from various causes. The anti-VEGF-D antibodies can be used for diagnosing diseases resulting from abnormal production of VEGF-D by quantifying VEGF-D.

BRIEF DESCRIPTION OF THE DRAWINGS

FIG. 2 compares the amino acid sequences of EST (H24828) and VEGF-C, SEQ ID NOS: 28 and 29, respectively.

FIG. 3 compares the amino acid sequences deduced from the VEGF-D gene and from the known genes of the VEGF family proteins, SEQ ID NOS: 1 and 29-34, respectively.

FIG. 4A shows the hydrophobicity plot of VEGF-D. FIG. 4B shows the prediction of the cleavage site of the VEGF-D signal peptide.

BEST MODE FOR IMPLEMENTING THE INVENTION

Figure 1:
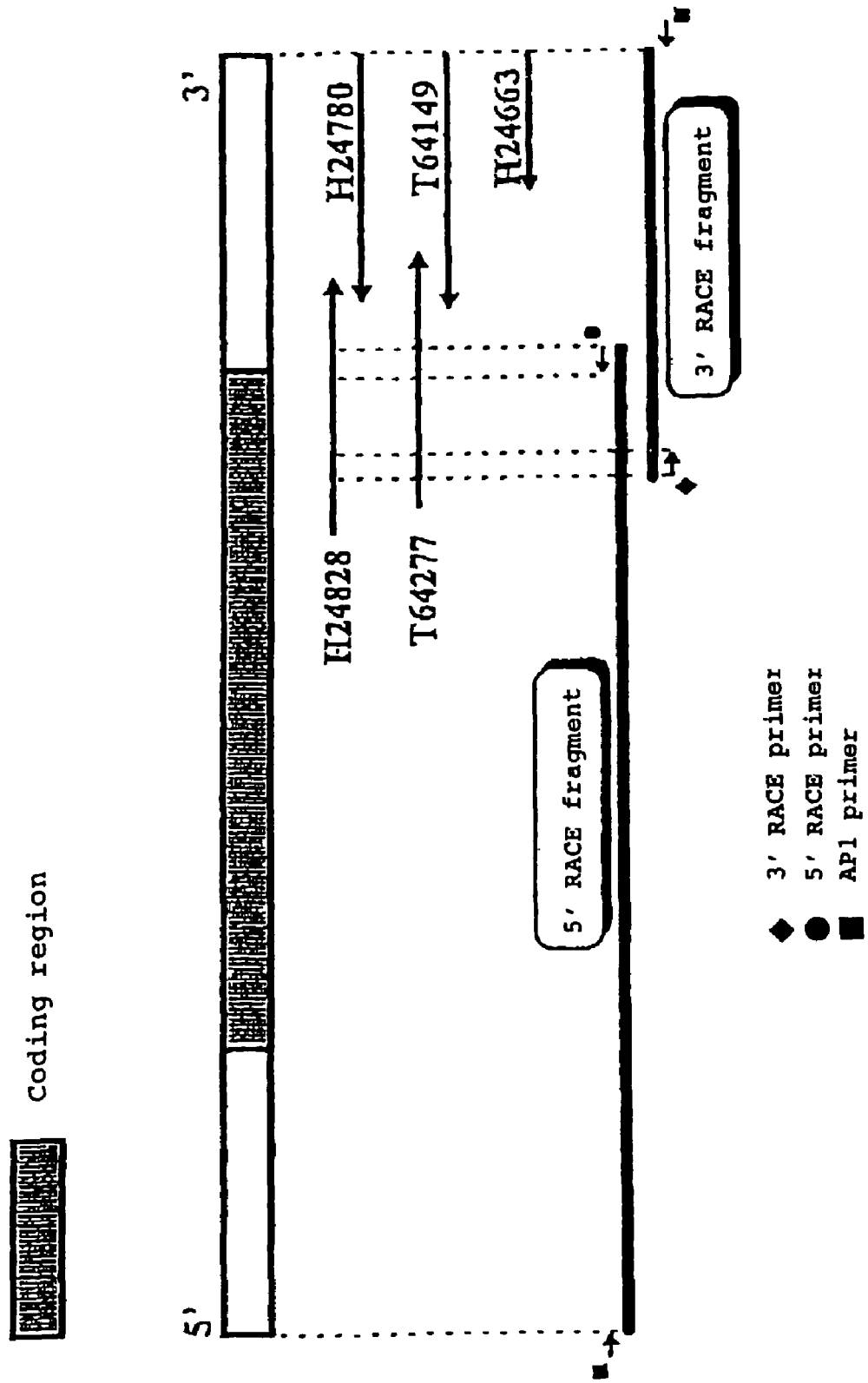
FIG. 1 shows the relationship among the VEGF-D gene, the EST sequences, and the primers used for cloning.

The following examples illustrate the present invention in detail, but are not to be construed to limit the scope of the invention.

Example 1

Homology Search by TFASTA Method

The sequence CGPNKELDENTCQCVC (SEQ ID NO. 3) was designed based on the consensus sequence found in the BR3P (Balbiani ring 3 protein) repeat at the C-terminus of VEGF-C. The entire ESTs and STS sequences in the Genbank database (as of 29 February 1996) were then searched by the TFASTA method (Person and Lipman, Proc. Natl. Acad. Sci. USA 85:2444-2448 (1988)). The searching conditions used are shown below (Table 1).

TABLE 1

| Sequences | 392,210 |
|---|---|
| Symbols | 135,585,305 |
| Word Size | 2 |
| Gap creation penalty | 12.0 |
| Gap extension penalty | 4.0 |

As a result, an EST (Accession No. H24828) that is considered to code the consensus sequence was found. The sequence is one of the ESTs registered by The WashU-Merck EST Project, and nine out of 16 amino acid residues were identical. Further searching for UniGene by NCBI based on this sequence revealed that five registered sequences (T64149, H24780, H24633, 124828, and T64277 (as of 1 March 1996)), including the above EST, were considered to be derived from the same gene. T64277 and T64149, as well as H24828 and H24780, are the combination of the 5'sequence and the 3'sequence of the same clones, and the length of the insert in both of these clones was 0.9 kb (FIG. 1).

Translating the H24828 sequence into a protein sequence, SEQ ID NO: 28., in a frame where homology is found suggested that this sequence codes 104 C-terminal amino acid residues. Comparing this amino acid sequence with the C-terminus of VEGF-C, 28 out of 104 amino acids (27%) were identical. Moreover, the amino acids that are important for maintaining the protein structure, such as cysteine and proline, were well conserved (FIG. 2). Conserved sequences are shown in a black box.

Example 2 cDNA Cloning from a Library

Primers for 5' RACE and 3' RACE (5' RACE primer: 5'-AGGGATGGGGAACTTGGAACGCTGAAT-3' (SEQ ID NO:4), 3' RACE primer: 5'-GATCTAATCCAGCAC-CCCAAAAACTGC-3' (SEQ ID NO:5) were designed (FIG. 1). A double-stranded cDNA was synthesized from human lung-derived polyA+RNA using reverse transcriptase. PCR was then performed using Marathon-Ready cDNA, Lung (Clontech), having an adapter cDNA ligated to both ends as a template cDNA, and using the above primer and adapter primer (AP-1 primer: 5'-CCATCCTAATACGACTCACTAT-AGGGC-3' (SEQ ID NO:6), FIG. 1) as primers. The above adapter cDNA contains the regions to which the adapter primers AP-1 and AP-2 hybridize. The PCR was performed in a manner such that the system was exposed to treatment at 94° C. for 1 min; five cycles of treatment at 94° C. for 30 sec and at 72° C. for 4 min; five cycles of treatment at 94° C. for 30 sec and at 70° C. for 4 min; then 25 cycles of treatment at 94° C. for 20 sec and at 68° C. for 4 min. (TaKaRa Ex Taq (Takara Shuzo) and the attached buffer were used as Taq polymerase instead of Advantage KlenTaq Polymerase Mix.) As a result, 1.5 kb fragments were amplified at the 5' region and 0.9 kb fragments at the 3' region. These fragments were cloned with the pCR-Direct Cloning System (Clontech), CR-TRAP Cloning System (GenHunter), and PT7Blue-T vector (Novagen). When the 5'-RACE fragment was cloned into the pCR-Direct vector, the fragment was amplified again using 5'-CTGGT-TCGGCCCAGAACTTGGAACGCTGAATCA-3'(SEQ ID NO:7) and 5'-CTCGCTCGCCCACTAATACGACTCAC-TATAGG-3'(SEQ ID NO:8) as primers.

Example 3

Nucleotide Sequence Analysis

ABI PRISM Dye Terminator Cycle Sequencing Ready Reaction Kit with Amplitaq DNA Polymerase FS and 377 A DNA Sequencer (ABI).were used for DNA sequencing. The primers used are the primers in the vectors (5'-AATTAAC-CCTCACTAAAGGG-3'(SEQ ID NO. 9), 5CCAGGGTTTTCCCAGTCACGAC-3'(SEQ ID NO. 10)), AP-2 primer (5ACTCACTATAGGGCTCGAGCGGC-3' (SEQ ID NO. 11)), and 10 primers in the sequence shown below (Table 2).

TABLE 2

| SQ1 | (SEQ ID NO. 12) | 5'-AAGTCTGGAGACCTGCT-3' |
|---|---|---|
| SQ2 | (SEQ ID NO. 13) | 5'-CAGCAGGTCTCCAGACT-3' |
| SQ3 | (SEQ ID NO. 14) | 5'-CGCACCCAAGGAATGGA-3' |
| SQ4 | (SEQ ID NO. 15) | 5'-TGACACCTGGCCATTCCA-3' |
| SQ5 | (SEQ ID NO. 16) | 5'-CATCAGATGGTAGTTCAT-3' |

TABLE 2-continued

| SQ6 | (SEQ ID NO. 17) | 5'-ATGCTGAGCGAGAGTCCATA-3' |
|---|---|---|
| SQ7 | (SEQ ID NO. 18) | 5'-CACTAGGTTTGCGGCAACTT-3' |
| SQ8 | (SEQ ID NO. 19) | 5'-GCTGTTGGCAAGCACTTACA-3' |
| SQ9 | (SEQ ID NO. 20) | 5'-GATCCATCCAGATCCCTGAA-3' |
| SQ10 | (SEQ ID NO. 21) | 5'-CAGATCAGGGCTGCTTCTA-3' |

Determining the nucleotide sequence of the 1.5 kb fragment at the 5'-side and the 0.9 kb fragment at the 3'-side revealed that the sequence of the overlapping region was identical, confirming that 5'- and 3'-side cDNAs of the desired gene were obtained. Determining the entire nucleotide sequence of the cDNA revealed that this novel gene has the full length of 2 kb and can code a protein consisting of 354 amino acid residues (SEQ ID NO:1 and SEQ ID NO:2). FIG. 1 shows the relation between this gene and the EST sequences registered in the Genbank database. Comparing the amino acid sequence with other VEGF family proteins revealed that the amino acids that are well conserved between family proteins are also conserved in this novel gene, and therefore this gene is obviously a new member of the VEGF family (FIG. 3). In FIG. 3, HSVEGF indicates human VEGF (SEQ ID NO: 33); HSVEGF-D, HSVEGF-C, and HSVEGF-B indicate human VEGF homologues (human VEGF-D (SEQ ID NO: 1), human VEGF-C (SEQ ID NO: 29), and human VEGF-B (SEQ ID NO: 34), respectively); HSPDGF-A indicates human PDGF-A (SEQ ID NO: 30); HSPDGF-B indicates human PDGF-B (SEQ ID NO: 31); and HSP1GF2 indicates human P1GF2 (SEQ ID NO: 32). The conserved sequences are shown in a black box. Since VEGF-D is highly homologous to VEGF-C that was cloned as the Flt4 ligand, it was presumed to be a ligand to a Flt-4-like receptor.

Deducing the signal peptide cleavage site (FIG. 4B) by hydrophobicity plot (FIG. 4A) and the method of von Heijne (von Heijne, G, Nucleic Acids Res. 14, 4683-4690 (1986)), N-terminal 21 amino acid residues may be cleaved as signal peptides, and they may also undergo additional processing like VEGF-C.

Example 4

Northern Blot Analysis

A 1kb fragment, which had been cut out by digestion with EcoRI from the 5'-fragment subcloned into pCR-Direct vector, was labeled with [α-$^{32}$P]dCTP and used as a probe. Labeling was performed by random priming using Ready-to Go DNA labeling beads (Pharmacia). Hybridization was performed in ExpressHyb Hybridization Solution (Clontech) by the usual method using Multiple Tissue Northern (MTN) Blot-Human, Human II, Human Fetal, and Human Cell lines (Clontech). Significant expression was observed in lung, heart, and intestine. Weak expression was observed in skeletal muscle, ovary, colon, and pancreas. The apparent molecular weight of the mRNA was 2.2 kb, and the cloned fragment seemed to be almost the full length of the gene.

Example 5

VEGF-D Protein Expression in *E. coli*

Two primers, 5'-TCCAGATCTTTTGCGGCAACTTC-TATGACAT-3(SEQ ID NO. 22) and 5'-CAGGTCGACT- CAAACAGGCACTAATTCAGGTAC-3(SEQ ID NO.23), were synthesized to amplify the region corresponding to the 89th to 181st amino acid residues of human VEGF cDNA. The thus-obtained DNA fragment was digested with restriction enzymes BglII and SalI, and ligated using ligation kit II (Takara Shuzo Co., Ltd) to plasmidpQE42 (QIAGEN), which had been digested with restriction enzymes BamHI and SalI. The resulting plasmid was introduced into E. coli SG19003 [pREP4] (QIAGEN), and aplasmid, which was obtained as designed without any mutation, was selected (pQE42-BS3). Plasmid pQE42-BS3 was introduced into E. coli BL21 (Invitorogen) and cultured in 10 ml of L Broth containing 100 mg/l bicucilline (ampicillin sodium for injection, Meiji Seika Kaisha, Ltd.). 200 ml of fresh L Broth was then inoculated with the culture. After incubation at 37° C. for 1.5 hours, IPTG was added to 3 mM, and the culture was further incubated at 37° C. for 5 hours. After cells were harvested, a protein was purified with a Ni-NTA column following the protocol of QIAexpress TypeII kit.

Example 6

Expression of DHFR-VEGF-D Fusion Protein in *E. coli*

The region corresponding to the 89th to 181st amino acid residues of human VEGF CDNA was amplified with the same primers used in Example 5. The thus-obtained DNA fragment was digested with restriction enzymes BglI and SalI. The fragment was then ligated using ligation kit II (Takara Shuzo Co., Ltd.) to the plasmid pQE40 (QIAGEN), which had been digested with restriction enzymes BamHI and SalI. The resulting plasmid was introduced into E. coli SG19003 [pREP4] (QIAGEN), andaplasmid, whichwas obtained as designed without any mutation, was selected (pQE40-BS3). Plasmid pQE40-BS3 was introduced into E. coli BL21 (Invitrogen) and cultured in 10 ml of L Broth containing 100 mg/i bicucilline (ampicillin sodium for injection, Meiji Seika Kaisha, Ltd.). 200 ml of fresh L Broth was then inoculated with the culture. After incubation at 37° C. for 1.5 hours, IPTG was added to 3mM, and the culture was further incubated at 37° C. for 5 hours. After cells were harvested, a DHFR-VEGF-D fusion protein was purified with a Ni-NTA column following the protocol of a QIAexpress TypeII kit.

Example 7

Cloning Mouse VEGF-D cDNA

Two Hybond-N+(Amersham) filters (20 cm×22 cm) on which 1.5×10$^5$ pfu of Mouse lung 5'-stretch cDNA library was transferred were prepared. Gradient hybridization from 68° C. to 55° C. was performed for 2 hours in ExpressHyb Hybridization Solution (Clontech) using as a probe an approximately 50 ng Pvu II fragment of human VEGF-D, which had been labeled with $\alpha^{32}$P-dCTP (Amersham) using Ready-To-Go DNA Labeling Beads(-dCTP) (Pharmacia). The filters were washed four times in 2×SSC, 0.05% SDS at room temperature for 10 min, then washed in 0.1×SSC, 0.1% SDS at 45° C. for 3 min. The washed filters were exposed overnight at −80° C. using HyperFilm MP (Amersham) and intensifying paper. Positive clones were subjected to the second screening in the same manner as above to isolate a single clone. Isolated lambda DNAs were purified from the plate lysate using a QIAGEN Lambda MAX I Kit (Qiagen). Insert DNAs were cut out with EcoRI and subcloned into pUC118 EcoRI/BAP (Takara Shuzo Co., Ltd.). Its nucleotide sequence was then determined with ABI377 sequencer (Perkin Elmer). The cDNA coding the full length of mouse VRGF-D was reconstructed with two of the obtained clones that overlapped each other. SEQ ID NO. 24 shows the nucleotide sequence of mouse VEGF-D cDNA and the deduced amino acid sequence therefrom.

Example 8

Cloning Rat VEGF-D cDNA

Two Hybond-N+(Amersham) filters (20 cm×22 cm), on which 1.5×10$^5$ pfu of Rat lung 5'-stretch cDNA library had been transferred, were prepared. Gradient hybridization from 68° C. to 55° C. was performed for 2 hours in ExpressH.Fyb Hybridization Solution (Clontech) using as a probe an approximately 1 µg fragment containing 1-782 bp of the mouse VEGF-D cDNA which had been labeled with $\alpha^{32}$P-dCTP (Amersham) using Ready-To-Go DNA Labeling Beads(-dCTP) (Pharmacia). The filters were washed four times in 2×SSC, 0.05% SDS at room temperature for 10 min, then washed in 0.1×SSC, 0.1% SDS at 45° C. for 3 min. The washed filters were exposed overnight at −80° C. using HyperFilmMP (Amersham) and intensifying paper. Positive clones were subjected to the second screening in the same manner as above to isolate a single clone. The isolated positive clone was excised into pBluescript using E. coli SOLAR (Stratagene) and helper phage ExAssist (Stratagene), then the sequence was determined with ABI377 sequencer (Perkin Elmer). The sequence seemed to be the rat VEGF-D cDNA but did not contain the termination codon.

To obtain the C-terminal cDNA which had not been obtained, PCR was performed using Marathon-Ready rat kidney cDNA (Clontech) as a template and 5'primerGCTGC-GAGTGTGTCTGTAAA (SEQ ID No. 26) and 3primer GGGTAGTGGGCAACAGTGACAGCAA (SEQ ID NO. 27) with 40 cycles of 94° C. for 15 sec, 55° C. for 30 sec, and 72° C. for 2 min. After the thus-obtained fragment was subcloned into pGEM-T vector (promega), the nucleotide sequence was determined with ABI377 sequencer (Perkin Elmer). The resulting clone contained the C-terminus of rat VEGF-D. Based on the results of sequencing the clone obtained by plaque hybridization and the clone obtained by PCR, the full length of the rat VEGF-D sequence was determined. SEQ ID NO. 25 shows the determined nucleotide sequence and the deduced amino acid sequence therefrom.

INDUSTRIAL APPLICABILITY

In the present invention, a novel protein (VEGF-D) having significant homology to VEGF-C and its gene have been isolated. VEGF-D appears to be involved in the pathological neovascularization associated with diabetes, rheumatoid arthritis, the growth of solid tumors, differentiation and proliferation of blood cells, formation of lymphatic vessels, and formation of edema resulting from various causes as well as the normal neovascularization at the developmental stage. The gene of the present invention can be used to diagnos disorders caused by abnormalities of the VEGF-D gene and gene therapy for the VEGF-D deficiency. The VEGF-D protein, which is obtained by expressing the gene of the present invention, can be used for healing wounds, promoting collateral vessel formation, and aiding hematopoietic stemcellproliferation. The antibodies or inhibitors against the VEGF-D protein can be used for treating angiodysplasia and lymphangiodysplasia associated with inflammation, edemas arising from various causes, dyshematopoiesis, and, as a novel anticancer agent, for treating pathological neovascularization. The VEGF-D protein and its antibodies can be useful for diagnosing diseases resulting from abnormal production of VEGF-D.

The invention claimed is:

1. An isolated DNA encoding a protein shown by SEQ ID NO: 1.

2. An isolated DNA that is capable of hybridizing with the complement of the DNA shown by SEQ ID NO: 2 under the conditions of hybridizing under a temperature gradient of 68° C. to 55° C. for 2 hours and washing with a 2×SSC solution containing 0.05% SDS at room temperature for 10 minute for four times and with a 0.1×SSC solution containing 0.1% SDS at 45° C. for 3 minutes and encodes a protein having at least one activity selected from the group consisting of: vascular formation, lymphatic vessel formation, pathological neovascularization, increasing vascular permeability, edema formation, wound healing, and promoting collateral vessel formation.

3. An isolated DNA having 90% or higher sequence homology to the DNA shown by SEQ ID NO: 2 and encoding a protein having at least one activity selected from the group consisting of: vascular formation, lymphatic vessel formation, pathological neovascularization, increasing vascular permeability, edema formation, wound healing, and promoting collateral vessel formation.

4. A vector containing the DNA of claim 1, 2 or 3.

5. An isolated host cell containing the vector of claim 4.

6. A method of producing a protein, wherein said method comprises the steps of: (a) culturing the host cell of claim 5 under conditions sufficient for protein expression, and
   (b) purifying the protein expressed in step (a).

* * * * *